(12) United States Patent
Han et al.

(10) Patent No.: US 9,839,552 B2
(45) Date of Patent: Dec. 12, 2017

(54) POWERED JOINT ORTHOSIS

(75) Inventors: Zhixiu Han, Acton, MA (US);
Christopher E. Barnhart, Carlisle, MA (US); Hugh M. Herr, Somerville, MA (US); Christopher Williams, Pittsburgh, PA (US); Jeff A. Weber, San Francisco, CA (US); Richard J. Casler, Jr., Lowell, MA (US)

(73) Assignee: BIONX MEDICAL TECHNOLOGIES, INC., Bedford, MA (US)

( * ) Notice: Subject to any disclaimer, the term of this patent is extended or adjusted under 35 U.S.C. 154(b) by 596 days.

(21) Appl. No.: 13/347,443

(22) Filed: Jan. 10, 2012

(65) Prior Publication Data
US 2012/0259429 A1    Oct. 11, 2012

Related U.S. Application Data

(60) Provisional application No. 61/431,277, filed on Jan. 10, 2011.

(51) Int. Cl.
*A61F 2/30*    (2006.01)
*A61F 5/01*    (2006.01)
*A61H 3/00*    (2006.01)

(52) U.S. Cl.
CPC ........... *A61F 5/0127* (2013.01); *A61H 3/008* (2013.01); *A61H 2201/123* (2013.01);
(Continued)

(58) Field of Classification Search
CPC ................. A61F 5/0127; A61H 3/008; A61H 2201/1647; A61H 2201/165;
(Continued)

(56) References Cited

U.S. PATENT DOCUMENTS 2,489,291 A    11/1949  Henschke at al.
2,529,968 A    11/1950  Sartin
(Continued)

FOREIGN PATENT DOCUMENTS

EP    1393866    3/2004
WO    WO-03068453    8/2003
(Continued)

OTHER PUBLICATIONS

Abbas J. and Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.
(Continued)

*Primary Examiner* — Quang D Thanh

(57) ABSTRACT

A powered device augments a joint function of a human during a gait cycle using a powered actuator that supplies an augmentation torque, an impedance, or both to a joint, and a controller that modulates the augmentation torque, the impedance, and a joint equilibrium according to a phase of the gait cycle to provide at least a biomimetic response. Accordingly, the device is capable of normalizing or augmenting human biomechanical function, responsive to a wearer's activity, regardless of speed and terrain.

29 Claims, 13 Drawing Sheets

(52) U.S. Cl.
CPC ............... *A61H 2201/1215* (2013.01); *A61H 2201/149* (2013.01); *A61H 2201/165* (2013.01); *A61H 2201/1647* (2013.01); *A61H 2201/5038* (2013.01); *A61H 2201/5069* (2013.01); *A61H 2201/5084* (2013.01); *A61H 2201/5097* (2013.01); *A61H 2205/106* (2013.01); *A61H 2205/12* (2013.01)

(58) Field of Classification Search
CPC .... A61H 2201/5038; A61H 2201/5069; A61H 2201/149; A61H 2201/5097; A61H 2201/1215; A61H 2201/123; A61H 2201/5084; A61H 2205/12; A61H 2205/106; A61H 2205/01
USPC .......... 601/5, 23, 27, 32, 33, 34, 35, 87, 98, 601/104; 602/5, 16, 23–29; 623/24, 26, 623/38, 52
See application file for complete search history.

(56) References Cited

U.S. PATENT DOCUMENTS

| | | |
|---|---|---|
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,898,948 A | 5/1999 | Kelly et al. |
| 5,910,720 A | 6/1999 | Williamson et al. |
| 5,932,230 A | 8/1999 | DeGrate |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |

(56) References Cited

U.S. PATENT DOCUMENTS

| | | |
|---|---|---|
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,628,766 B1 * | 12/2009 | Kazerooni ............... A61F 5/00 601/35 |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,998,221 B2 | 8/2011 | Lecomte et al. |
| 8,002,724 B2 | 8/2011 | Hu et al. |
| 8,007,544 B2 | 8/2011 | Jonsson et al. |
| 1,022,480 A1 | 9/2011 | Clausen at al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 1,024,593 A1 | 10/2011 | Clausen at al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,202,325 B2 | 6/2012 | Albrecht-Laatsch et al. |
| 2001/0029400 A1 | 10/2001 | Deffenbaugh et al. |

(56) References Cited

U.S. PATENT DOCUMENTS

| | | | |
|---|---|---|---|
| 2002/0052663 | A1 | 5/2002 | Herr et al. |
| 2002/0092724 | A1 | 7/2002 | Koleda |
| 2002/0138153 | A1 | 9/2002 | Koniuk |
| 2003/0093021 | A1 | 5/2003 | Goffer |
| 2003/0125814 | A1 | 7/2003 | Paasivaara et al. |
| 2003/0139783 | A1 | 7/2003 | Kilgore et al. |
| 2003/0163206 | A1 | 8/2003 | Yasui et al. |
| 2003/0195439 | A1 | 10/2003 | Caselnova |
| 2004/0039454 | A1 | 2/2004 | Herr et al. |
| 2004/0049290 | A1 | 3/2004 | Bedard |
| 2004/0054423 | A1 | 3/2004 | Martin |
| 2004/0064195 | A1 | 4/2004 | Herr |
| 2004/0088025 | A1 | 5/2004 | Gesotti |
| 2004/0181118 | A1 | 9/2004 | Kochamba |
| 2005/0049652 | A1 | 3/2005 | Tong |
| 2005/0059908 | A1 | 3/2005 | Bogert |
| 2005/0070834 | A1* | 3/2005 | Herr et al. ............... 602/28 |
| 2005/0085948 | A1 | 4/2005 | Herr et al. |
| 2005/0155444 | A1 | 7/2005 | Otaki et al. |
| 2006/0004307 | A1 | 1/2006 | Horst |
| 2006/0069448 | A1 | 3/2006 | Yasui |
| 2006/0094989 | A1 | 5/2006 | Scott et al. |
| 2006/0135883 | A1 | 6/2006 | Jonsson et al. |
| 2006/0173552 | A1 | 8/2006 | Roy |
| 2006/0224246 | A1* | 10/2006 | Clausen et al. ............ 623/24 |
| 2006/0249315 | A1 | 11/2006 | Herr et al. |
| 2006/0258967 | A1 | 11/2006 | Fujil et al. |
| 2006/0276728 | A1 | 12/2006 | Ashihara et al. |
| 2007/0016329 | A1* | 1/2007 | Herr et al. ............... 700/250 |
| 2007/0043449 | A1 | 2/2007 | Herr et al. |
| 2007/0123997 | A1 | 5/2007 | Herr et al. |
| 2007/0162152 | A1 | 7/2007 | Herr et al. |
| 2008/0114272 | A1 | 5/2008 | Herr et al. |
| 2008/0155444 | A1 | 6/2008 | Pannese et al. |
| 2009/0030530 | A1 | 1/2009 | Martin |
| 2009/0171469 | A1* | 7/2009 | Thorsteinsson et al. ....... 602/16 |
| 2009/0222105 | A1 | 9/2009 | Clausen |
| 2010/0025409 | A1 | 2/2010 | Hunter |
| 2010/0114329 | A1 | 5/2010 | Casler et al. |
| 2010/0179668 | A1 | 7/2010 | Herr et al. |
| 2010/0312363 | A1 | 12/2010 | Herr et al. |

FOREIGN PATENT DOCUMENTS

| | | | |
|---|---|---|---|
| WO | WO-2004017872 | | 3/2004 |
| WO | WO-2004019832 | | 3/2004 |
| WO | WO-2006110895 | | 10/2006 |
| WO | WO-2009082249 | | 7/2009 |
| WO | WO-2010025409 | | 3/2010 |
| WO | WO-2010027968 | | 3/2010 |
| WO | WO 2010/048928 | * | 5/2010 ............ H02K 21/24 |

OTHER PUBLICATIONS

Abul-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis—hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44, No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003). 88 pages.

Blickhan, R., "The spring-mass model for running and hopping," J of Biomech. 22, Feb. 1989, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

Brockway, J., "Derivation of formulae used to calculate energy expenditure in man," Human Nutrition Clinical Nutrition, vol. 41, Nov. 1987, pp. 463-471.

Brown, R., "On the nature of the fundamental activity of the nervous centres: together with an analysis of the conditioning of rhythmic activity in progression, and a theory of the evolution of function in the nervous system," J Physiol, vol. 48, No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences The Americal Journal of Gastronenterology, vol. 105, No. 4, Apr. 2010, pp. 866-875.

Chu, A., Kazerooni, H. and Zoss, A., "On the Biomimetic Design of the Berkeley Lower Extremity Exoskeleton (BLEEX)," Proceedings of the 2005 IEEE International Conference on Robotics and Automation, Apr. 2005, Barcelona, Spain, pp. 4356-4363.

Colborne, G. R., S. Naumann, P. E. Langmuir, and D. Berbrayer, "Analysis of mechanical and metabolic factors in the gait of congenital below knee amputees," Am. J. Phys. Med. Rehabil., vol. 92, pp. 272-278, Oct. 1992.

Collins, et al., "Controlled Energy Storage and Return Prosthesis Reduces Metabolic cost of Walking," ASB 29th Annual Meeting, Cleveland, Ohio, Jul. 31-Aug. 5, 2005, 1 page.

(56) References Cited

OTHER PUBLICATIONS

Collins, et al., "Supporting Online Material for Efficient bipedal robots based on passivedynamic walkers," Mechanical Engineering, University of Michigan, Feb. 2005, Ann Arbor, MI, pp. 1-8.
Crago P., et. al., "New Control Strategies for neuroprosthetic systems," Journal of Rehabilitation Research and Development, vol. 33, No. 2, Apr. 1996, pp. 158-172.
Daley, M.A., Felix, G., Biewener, A. A., 2007. Running stability is enhanced by a proximodistal gradient in joint neuromechanical control. J Exp Bioi 210 (Pt 3), Nov. 2006, pp. 383-394.
Dapena, J. and McDonald, C., "Three-dimensional analysis of angular momentum in the hammer throw," Med. Sci. in Sports Exerc., vol. 21, No. 2, Apr. 1989, pp. 206-220.
Dietz, V., "Proprioception and locomotor disorders," Nat Rev Neurosci, vol. 3, Oct. 2002, pp. 781-790.
Dietz, V., "Spinal Cord Pattern Generators for Locomotion," download Feb 6, 2012, http://www.Clinph-journal.com/article/PIIS1388245703001202/fulltext, 12 pages.
Doerschuk, et. al., "Upper extremity limb function discrimination using EMG signal analysis," IEEE Transactions on Biomedical Engineering. vol. 30., No. 1., Jan. 1983, pp. 18-28.
Doke, J., et. al., "Mechanics and energetics of swinging the human leg," The Journal of Experimental Biology, vol. 208, Feb. 2005, pp. 439-445.
Dollar, et al., "Lower Extremity Exoskeletons and Active Orthoses: Challenges and State-of-the-Art," IEEE Transactions on Robotics, vol. 24, No. 1, Feb. 2008, 15 pages.
Donelan, J., et. al., "Force regulation of ankle extensor muscle activity in freely walking cats," J Neurophysiol, vol. 101, No. 1, Nov. 2008, pp. 360-371.
Donelan, J., et. al., "Mechanical work for step-to-step transitions is a major determinant of the metabolic cost of human walking," J. Exp. Bioi., vol. 205, Dec. 2002, pp. 3717-3727.
Donelan, J., et. al. "Simultaneous positive and negative external mechanical work in human walking," Journal of Biomechanics, vol. 35, Jan. 2002, pp. 117-124.
Drake, C., "Ankle & Foot Splints or Orthoses," HemiHelp, Information Sheet 13 Last updated Jun. 2009, 5 pages.
Drake, C., "Ankle & Foot Splints or Orthoses (AFOs)," HemiHelp, Last updated Jun. 2009, 8 pages.
Eilenberg, M., "A Neuromuscular-Model Based Control Strategy for Powered Ankle-Foot Prostheses," Masters Thesis, Massachusetts Institute of Technology, Cambridge, Mass., 2009.
Ekeberg, 0. and Grillner, S., "Simulations of neuromuscular control in lamprey swimming," Philos Trans R Soc Land B Bioi Sci, vol. 354, May 1999, pp. 895-902.
Ekeberg, 0. and Pearson, K., "Computer simulation of stepping in the hind legs of the cat: an examination of mechanisms regulating the stance-to-swing transition," J Neurophysiol, vol. 94, No. 6, Jul. 2005, pp. 4256-4268.
Endo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.
Eppinger, S. Seering W., "Three dynamic problems in robot force control," IEEE Transactions on Robotics and Automation, vol. 8, No. 6, Dec. 1992, pp. 751-758.
Esquenazi, A. and DiGiacomo, R., "Rehabilitation After Amputation," Journ Am Podiatr Med Assoc, vol. 91, No. 1, Jan. 2001, pp. 13-22.
Farley, C. and McMahon, T., "Energetics of walking and running: insights from simulated reduced-gravity experiments," The American Physiological Society, Dec. 1992, pp. 2709-2712.
Farry, K. A., et al., "Myoelectric teleoperation of a complex robotic hand," IEEE Transactions on Robotics and Automation. vol. 12, No. 5, Oct. 1996, pp. 775-788.
Featherstone, R., 1987, "Robot Dynamic Algorithms", Boston, Mass., Kluwer Academic Publishers, pp. 155-172.

File, K., et. al., "Design and Control of an Electrically Powered Knee Prosthesis," Proc. of 2007 IEEE 10th International Conference on Rehabilitation Robotics (ICORR), Jun. 2007, pp. 902-905.
Flowers, W. "A Man-Interactive Simulator System for Above-Knee Prosthetic Studies," Ph.D. thesis, Massachusetts of Institute Technology, Department of Mechanical Engineering. Jul. 10, 1973.
Fod, A., et. al., "Automated Derivation of Primitives for Movements Classification," Autonomous Robots, vol. 12, No. 1, Jan. 2002, pp. 39-54.
Frigon, A. and Rossignol, S., "Experiments and models of sensorimotor interactions during locomotion," Bioi Cybern, vol. 95, No. 6, Nov. 2006, pp. 607-627.
Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.
Fukuda, 0. et al., "A human-assisting manipulator teleoperated by EMG signals and arm motions," IEEE Transactions on Robotics and Automation. vol. 19, No. 2, Apr. 2003, pp. 210-222.
Gates, D., "Characterizing ankle function during stair ascent, descent, and level walking for ankle prosthesis and orthosis design," Masters thesis, Boston University, 2004, pp. 1-82.
Geiritsen, K., et. al., "Direct dynamics simulation of the impact phase in heel-toe running," J. Biomech., vol. 28, No. 6, Jun. 1995, Great Britain, pp. 661-668.
Geyer, H., et. al., "Compliant leg behaviour explains the basic dynamics of walking and running," Proc. R. Soc. Cond. B 273, Aug. 2006, pp. 2861-2867.
Geyer, H., et. al., "Positive force feedback in bouncing gaits?," Proceedings of Royal Society B—Biological Sciences, vol. 270, No. 1529, Aug. 2003, pp. 2173-2183, 2003.
Geyer, H. and Herr H., "A muscle-reflex model that encodes principles of legged mechanics predicts human walking dynamics and muscle activities," IEEE Transactions on Neural Systems and Rehabilitations Engineering, vol. 18, No. 3, Jun. 2010, pp. 263-273.
Ghigliazza, R., et. al., "A simply stabilized running model," SIAM J. Applied. Dynamical Systems, vol. 2, No. 2, May 2004, pp. 187-218.
Godha, el al., "Integrated GPS/INS System for Pedestrian Navigation in a Signal Degraded Environment," ION GNSS, Sep. 2006, Fort Worth, TX, pp. 1-14.
Goswami, A., "Postural stability of biped robots and the footrotation indicator (FRI) point," International Journal of Robotics Research, vol. 18, No. 6, Jun. 1999, pp. 523-533.
Goswami, A. and Kallem, V., "Rate of change of angular momentum and balance maintenance of biped robots," Proceedings of the 2004 IEEE International Conference on Robotics and Automation, Apr. 2004, New Orleans, LA., pp. 3785-3790.
Graupe, D., et al., "A microprocessor system for multifunctional control of upper-limb prostheses via myoelectric signal identification," IEEE Transaction on Automatic Control. vol. AC-23, vol. 4, Aug. 1978, pp. 538-544.
Gregoire, L., and et al, "Role of mono- and bi-articular muscles in explosive movements," International Journal of Sports Medicine 5, 614-630. Dec. 1984.
Grillner, S. and Zangger, P., "On the central generation of locomotion in the low spinal cat," Exp Brain Res, vol. 34, No. 2, Jan. 1979, pp. 241-261.
Grimes, D. L., "An active multi-mode above-knee prosthesis controller," Ph.D. Thesis, Massachusetts Institute of Technology, Jul. 20, 1979.
Gu, W., "The Regulation of Angular Momentum During Human Walking," Undergraduate Thesis, Massachusetts Institute of Technology, Physics Department, Jun. 2003, pp. 2-48.
Gunther, M., et. al., "Human leg design: optimal axial alignment under constraints," J. Math. Bioi., vol. 48, Mar. 2004, pp. 623-646.
Gunther, M. and Ruder, H., "Synthesis of two-dimensional human walking: a test of the Amodel," Bioi. Cybern., vol. 89, May 2003, pp. 89-106.
Hanafusa et al., "A Robot Hand with Elastic Fingers and Its Application to Assembly Process," pp. 337-359, Robot Motion, Brady et al., MIT Press, Cambridge, MA, 1982.

(56) References Cited

OTHER PUBLICATIONS

Hansen, A. H., Childress, D. S., Miff, S.C., Gard, S. A., Mesplay, K. P., "The human ankle during walking: implication for the design of biomimetic ankle prosthesis," Journal of Biomechanics, vol. 37, No. 10, Oct. 2004, pp. 1467-1474.
Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.
Heglund, N., "A Simple Design for a Force-Plat to Measure Ground Reaction Forces," J. Exp. Bioi., vol. 93, Aug. 1981, pp. 333-338.
Herr, H. and McMahon, T.,"A trotting horse model," Int. J. Robotics Res., vol. 19, No. 6, Jun. 2000, pp. 566-581.
Herr, H. and Popovic, M., "Angular momentum regulation in human walking," J. Exp. Bioi., vol. 211, Feb. 2008, pp. 467-481.
Herr, H. and Wilkenfeld A., "User-adaptive control of a magnetorheologicalprosthetic knee," Industrial Robot: An International Journal, vol. 30, No. 1, 2003, pp. 42-55.
Herr, H., et. al, "A model of scale effects in mammalian quadrupedal running," J Exp Bioi 205 (Pt 7), Apr. 2002, pp. 959-967.
Heyn et al., "The Kinematice of the Swing Phase Obtained from Accelerometer and Gyroscope Measurements," 18th Annual International Conference of the IEEE Engineering in Medicine and Biology Society, Nov. 1996, Amsterdam, Netherlands, pp. 463-464.
Hill, V., "The heat of shortening and the dynamic constants of muscle," Proceedings of the Royal Society London B, vol. 126, No. 843, Oct. 1938, pp. 136-195.
Hirai, K., et al., "The development of Honda humanoid robot," Proceedings on IEEE/RSJ International Conference on Intelligent Robots and Systems, May 1998, Leuven, Belgium, pp. 1321-1326.
Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp. 2939-2945, Sep. 2007.
Hof. A., et. al., "Calf muscle moment, work and efficiency in level walking; role of series elasticity," Journal of Biomechanics, vol. 16, No. 7, Sep. 1983, pp. 523-537.
Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.
Hofbaur, M. and Williams, B., "Mode Estimation of Probabilistic Hybrid Systems", HSSC 2002, LNCS 2289, Mar. 25, 2002, pp. 253-266.
Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.
Hofmann, A., et. al., "Robust Execution of Bipedal Walking Tasks from Biomechanical Principles," Doctor of Philosophy at the Massachusetts Institute of Technology, Jan. 2006, 407 pages.
Hogan, N and Buerger S., "Impedance and Interaction Control," Robotics and Automation Handbook, CRC Press, Jun. 2004, pp. 19.1-19.24.
Hogan, N. (1976) A review of the methods of processing EMG for use as a proportional control signal. Biomedical Engineering. pp. 81-86.
Hogan, N., "Impedance Control: An Approach to Manipulation: Part I—Theory," Journal of Dynamic Systems, Measurement, and Control, vol. 107, Mar. 1985, pp. 1-7.
Hogan, N., "Impedance Control: An Approach to Manipulation: Part II—Implementation, " Journal of Dynamic Systems, Measurement , and Control, 107:8-16, (1985).
Hogan, N., Impedance Control: An Approach to Manipulation: Part III—Application, Journal of Dynamics Systems, Measurement, and Control, 107:17-24, (1985).
Hogan, N., "Impedance Control: An Approach to Manipulation," Dept. of Mechanical Engineering and Laboratory of Manufacturing and Productivity, Massachusetts Institute of Technology, Cambridge MA, pp. 304-313, (Jun. 1984).
Hollander, K. W., T. G. Sugar, and D. E. Herring, "Adjustable robotic tendon using a 'Jack Spring' .TM.," Proceedings on IEEE International Conference on Rehabilitation Robotics, Chicago, pp. 113-118, Jun. 28, 2005.
Howard, "Joint and Actuator Design for Enhanced Stability in Robotic Force Control," Ph.D. thesis, Massachusetts Inst. of Technology, Dept. of Aeronautics and Astronautics, Sep. 19, 1990.
Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.
Huang, Q., "Planning walking patterns for a biped robot," IEEE Transactions on Robotics and Automation, vol. 17, No. 3, Jun. 2001, pp. 280-289.
Hultborn, H., Spinal reflexes, mechanisms and concepts: from Eccles to Lundberg and beyond, Prog Neurobiol, vol. 78, Feb. 2006, pp. 215-232.
Ijspeert, A. J., 2008, "Central pattern generators for locomotion control in animals and robots: a review," Neural Netw, vol. 21, No. 4, May 2008, pp. 642-653.
Ijspeert, A., et. al., "From swimming to walking with a salamander robot driven by a spinal cord model," Science, vol. 315, No. 5817, Mar. 2007, pp. 1416-1420.
International Search Report and Written Opinion for PCT/US2009/055600 mailed Apr. 29, 2010 (23 pages).
International Search Report and Written Opinion for PCT/US2010/047279 mailed Jan. 19, 2011 (11 pages).
International Search Report and Written Opinion for PCT/US2011/031105 mailed Oct. 11, 2011 (16 pages).
International Search Report for PCT/US2012/020775 mailed Jun. 1, 2012 (6 pages).
International Search Report for PCT/US2012/021084 mailed Aug. 1, 2012 (3 pages).
International Search Report for PCT/US2012/022217 mailed May 31, 2012 (6 pages).
Ivashko, D., et. al, "Modeling the spinal cord neural circuitry controlling cat hindlimb movement during locomotion," Neurocomputing, vol. 52-54, Mar. 2003, pp. 621-629.
Johansson, J., et al., "A clinical comparison of variable damping and mechanically passive prosthetic knee devices," American Journal of Physical Medicine & Rehabilitation, vol. 84, No. 8, Aug. 2005, pp. 563-575.
Johnson, C. and Lorenz R., "Experimental identification of friction and its compensation in precise, position controlled mechanisms," IEEE Trans. on Industry Applications, vol. 28, No. 6, Dec. 1992, pp. 1392-1398.
Jonic S, et. al., "Three machine learning techniques for automatic determination of rules to control locomotion," IEEE Trans Biomed Eng, vol. 46, No. 3, Mar. 1999, pp. 300-310.
Kadaba, M., et. al., "Measurement of lower extremity kinematics during level walking," J. Orthop. Res., vol. 8, May 1990, pp. 383-392.
Kadaba, M., et. al., "Repeatability of kinematic, kinetic, and electromyographic data in normal adult gait," J. Orthop. Res., vol. 7, Nov. 1989, pp. 849-860.
Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.
Kajita, S., et. al., "A Hop towards Running Humanoid Biped," Proceedings of the 2004 IEEE International Conference on Robotics and Automation, Apr. 2004, New Orleans, LA., pp. 629-635.
Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.
Kaneko, K., et al., "Humanoid robot HRP-2," Proc. IEEE Int. Conf. on Robotics and Automation, Apr. 2004, New Orleans, La., pp. 1083-1090.
Kapti, A. and Yucenur M., "Design and control of an active artificial knee joint," Mechanism and Machine Theory, vol. 41, Apr. 2006, pp. 1477-1485.

(56) References Cited

OTHER PUBLICATIONS

Katie, D. and Vukobratovic, M., "Survey of intelligent control techniques for humanoid robots," Journal of Intelligent and Robotics Systems, vol. 37, Jun. 2003, pp. 117-141.
Kerrigan, D, et. al., "A refined view of the determinants of gait: significance of heel rise," Arch. Phys. Med. Rehab., vol. 81, Aug. 2000, pp. 1077-1080.
Kerrigan, D, et. al., "Quantification of pelvic rotation as a determinant of gait," Arch. Phys. Med. Rehab., vol. 82, Feb. 2001, pp. 217-220.
Khatib, 0., et. al., "Coordination and decentralized cooperation of multiple mobile manipulators," Journal of Robotic Systems, vol. 13, No. 11, Nov. 1996, pp. 755-764.
Khatib, 0., et. al., "Whole body dynamic behavior and control of human-like robots," International Journal of Humanoid Robotics, vol. 1, No. 1, Mar. 2004, pp. 29-43.
Kidder, et al., "A System for the Analysis of Foot and Ankle Kinematics During Gait," IEEE Transactions on Rehabilitation Engineering, vol. 4, No. 1, Mar. 1996, pp. 25-32.
Kim, et al., "Realization of Dynamic Walking for the Humaniod Robot Platform KHR-1," Advanced Robotics, vol. 18, No. 7, pp. 749-768, (2004).
Kirkwood C, et. al., "Automatic detection of gait events: a case study using inductive learning techniques.," J Biomed Eng, vol. 11, Nov. 1989, pp. 511-516.
Kitayama, I., Nakagawa N, Amemori K, "A microcomputer controlled intelligent A/K prosthesis," Proceedings of the 7th' World Congress of the International Society for Prosthetics and Orthotics, Chicago. Jun. 28, 1992.
Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.
Klute, et al., "Artificial Muscles: Actuators for Biorobotic Systems," The International Journal of Robotics Research, vol. 21, No. 4, Apr. 2002, pp. 295-309.
Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, et al., Intelligent Transtibial Prostheses with Muscle-Like Actuators,: 2002 American Physiological Society Intersociety Meeting: The Power of Comparative Physiology: Evolution, Integration, and Applied, 1 page.
Klute, et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, et al., "McKibben Artificial Muscles: Pneumatic Actuators with Biomechanical Intelligence," IEEE/ASME 1999 International Conference on Advanced Intelligent Mechatronics, Atlanta, GA, Sep. 19-22, 1999, pp. 221-226.
Klute, et al., "Muscle-Like Pneumatic Actuators for Below-Knee Prostheses," Actuator2000:7th International Conference on New Actuators, Bremen, Germany on Jun. 9-21, 2000, pp. 289-292.
Klute et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., Oct. 1-3, 1998, p. 52.
Klute, G., et al., "Mechanical properties of prosthetic limbs adapting to the patient," Journal of Rehabilitation Research and Development, vol. 38, No. 3, May 2001, pp. 299-307.
Koganezawa, K. and Kato, 1., "Control aspects of artificial leg," IFAC Control Aspects of Biomedical Engineering, 1987, pp. 71-85.
Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.

Kostov A., et. al., "Machine learning in control of functional electrical stimulation (FES) systems for locomotion," IEEE Trans on Biomed Eng, vol. 42, No. 6, Jun. 1995, pp. 541-551.
Kuo, A., "A simple model of bipedal walking predicts the preferred speed-step length relationship," Journal of Biomechanical Engineering, vol. 123, Jun. 2001, pp. 264-269.
Kuo, A., "Energetics of actively powered locomotion using the simplest walking model," Journal of Biomechanical Engineering, vol. 124, Feb. 2002, pp. 113-120.
LaFortune, "Three-Dimensional Acceleration of the Tibia During Walking and Running," J. Biomechanics, vol. 24, No. 10, 1991, pp. 877-886.
LeBlanc, M. and Dapena, J., "Generation and transfer of angular momentum in the javelin throw," Presented at the 20th annual meeting of the American Society of Biomechanics, Oct. 1996, Atlanta, Ga., pp. 17-19.
Li, C., et al. (Jun. 25, 2006) Research and development of the intelligently-controlled prosthetic ankle joint. Proc. of IEEE Int. Conf. on Mechatronics and Automation. Luoyang, China, pp. 1114-1119.
Liu, X., Low, K. H., Yu, H. Y., Sep. 2004 'Development of a Lower Extremity Exoskeleton for Human performance Enhancement', IEEE Conf. on Intelligent Robots and Systems, Sendai, Japan.
Lloyd R. and Cooke C., "Kinetic changes associated with load carriage using two rucksack designs," Ergonomics, vol. 43, No. 9, Sep. 2000, pp. 1331-1341.
Luinge, "Inertial Sensing of Human Movement," Twente University Press, ISBN 9036518237, 2002, pp. 1-80.
Lundberg, A., Oct. 19, 1968. Reflex control of stepping. In: The Nansen memorial lecture V, Oslo: Universitetsforlaget, 5-42.
Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.
Maganaris, C., "Force-length characteristics of in vivo human skeletal muscle," Acta Physiol. Scand., vol. 172, Aug. 2001, pp. 279-285.
Maganaris, C., "Force-length characteristics of the in vivo human gastrocnemius muscle," Clin. Anal., vol. 16, May 2003, pp. 215-223.
Martens, W.L.J., "Exploring the Information Content and Some Applications of Body Mounted Piezo-Resistive Accelerometers," in: P.H. Veltink and R.C. van Lummel (eds.), Dynamic Analysis using Body Fixed Sensors, ISBN 90-9007328-0, 1994, pp. 8-11.
Maufroy, C., Towards a general neural controller for quadrupedal locomotion, Neural Netw, vol. 21, No. 4, Apr. 2008, pp. 667-681.
Mayagoitia R., et al., "Accelerometer and rate gyroscope measurement of kinematics: an inexpensive alternative to optical motion analysis systems," Journal of Biomechanics, vol. 35, Apr. 2002, pp. 537-542.
McFadyen, B. and Winter, D., "An integrated biomechanical analysis of normal stair ascent and descent," Journal of Biomechanics, vol. 21, No. 9, 1988, Great Britain, pp. 733-744.
McGeer T., "Passive Dynamic Walking," International Journal of Robotics, vol. 9, No. 2, May 1988, pp. 62-82.
McGeer, T., "Principles of walking and running," Advances in Comparative and Environmental Physiology, vol. 11, Ch. 4, Apr. 1992, pp. 113-139.
Mcintosh, A., et. al., "Gait dynamics on an inclined walkway," Journal of Biomechanics, vol. 39, Sep. 2005, pp. 2491-2502.
McMahon, T., "The mechanics of running: how does stiffness couple with speed?," J. of Biomecb., vol. 23, 1990, pp. 65-78.
McMahon, T., et. al., "Groucho Running," Journal of Applied Physiology, vol. 62, No. 6, Jun. 1987, pp. 2326-2337.
Minassian, K., et. al., "Human lumbar cord circuitries can be activated by extrinsic tonic input to generate locomotor-like activity," Hum. Mov. Sci., vol. 26, Mar. 2007, pp. 275-295.
Mochon, S., et. al., "Ballistic walking," Journal of Biomechanics, vol. 13, Dec. 1980, pp. 49-57.
Molen, N., "Energy/speed relation of below-knee amputees walking on motor-driven treadmill," Int. Z. Angew. Physio, vol. 31, Mar. 1973, pp. 173.

(56) References Cited

OTHER PUBLICATIONS

Morris, "Accelerometry—A Technique for the Measurement of Human Body Movements," J. Biomechanics, vol. 6, Nov. 1973, pp. 729-736.

Muraoka, T., et. al, "Muscle fiber and tendon length changes in the human vastus lateralis during slow pedaling," J. Appl. Physiol., vol. 91, Nov. 2001, pp. 2035-2040.

Nakagawa A., "Intelligent Knee Mechanism and the Possibility to Apply the Principle to the Other Joints," Proceedings of the 20th Annual International Conference of the IEEE Engineering in Medicine and Biology Society, Vo. 20, No. 5, Oct. 1998, pp. 2282-2287.

Neal R. and Hinton G., "A view of the EM algorithm that justifies incremental, sparse, and other variants," in Michael I. Jordan (editor), Learning in Graphical Models, 1999, Cambridge, MA, pp. 1-14.

Ng, et al., "Fuzzy Model Identification for Classification of Gait Events in Paraplegics," IEEE Transactions on Fuzzy Systems, vol. 5, No. 4, Nov. 1997, pp. 536-544.

Nielsen, D., et. al., "Comparison of energy cost and gait efficiency during ambulation in below-knee amputees using different prosthetic feet—a preliminary report," Journal of Prosthetics & Orthotics, vol. 1, No. 1, 1989, pp. 24-29.

Oda, T, Ketal., 2005, "In vivo length-force relationships on muscle fiver and muscle tendon complex in the tibialis anterior muscle." Int. J. Sport and Health Sciences 3, 245-252.

Ogihara, N. and Yamazaki, N., "Generation of human bipedal locomotion by a bio-mimetic neuro-musculo-skeletal model," Bioi Cybern, vol. 84, No. 1, Jan. 2001, pp. 1-11.

Palmer, M., "Sagittal plane characterization of normal human ankle function across a range of walking gait speeds," Master's Thesis, MIT, Feb. 2002, Cambridge, MA, pp. 1-71.

Paluska, D., and Herr, H., "Series Elasticity and Actuator Power Ouput," Proceedings of the 2006 IEEE International Conference on Robotics and Automation, May 2006, Orlando, FL, pp. 1830-1833.

Paluska, D., and Herr, H., "The effect of series elasticity on actuator power and work output: implications for robotic and prosthetic joint design," Robotics and Autonomous Systems, vol. 54, Jun. 2006, pp. 667-673.

Pang, M., et. al., "The initiation of the swing phase in human infant stepping: importance of hip position and leg loading," J Physiol, vol. 528, No. 2, Oct. 2000, pp. 389-404.

Pasch, K. A., and W. P. Seering, "On the drive systems for high performance machines," AMSE J. Mechanisms, Transmissions, and Automation in Design vol. 106, pp. 102-108, Mar. 1984.

Paul, C., et. al., "Development of a human neuro-musculo-skeletal model for investigation of spinal cord injury," Bioi Cybern, vol. 93, No. 3, Aug. 2005, pp. 153-170.

Pearson, K., "Generating the walking gait: role of sensory feedback," Prog Brain Res, vol. 143, 2004, pp. 123-129.

Pearson, K., et. al., "Assessing sensory function in locomotor systems using neuro-mechanical simulations," Trends Neurosci, vol. 29, No. 11, Nov. 2006, pp. 625-631.

Perry, Gait Analysis: Normal and Pathological Function, New Jersey: SLACK Inc.; 1992, Book Review, 1 page.

Perry, J. and S. Shanfield, "Efficiency of dynamic elastic response prosthetic feet," Journal of Rehabilitation Research and Development, vol. 30, No. 1, 1993 pp. 137-143.

Petrofshy et al., "Feedback Control System for Walking in Man," Comput. Bioi. Med., vol. 14, No. 2, Mar. 1984, pp. 135-149.

Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.

Popovic, et al., "Gait Identification and Recognition Sensor," Proceedings of 6th Vienna International Workshop on Functional Electrostimulation, Sep. 1998, pp. 1-4.

Popovic, D., "Control of Movement for the Physically Disabled," Springer-Verlag London Limited, May 2000, pp. 270-302.

Popovic D., et al., "Control Aspects of Active Above-Knee Prosthesis," Int. Journal Man-Machine Studies, (1991) 35, pp. 751-767.

Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.

Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.

Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.

Popovic, M., et. al., "Ground Reference Points in Legged Locomotion: Definitions, Biological Trajectories and Control Implications," International Journal of Robotics Research, Dec. 2006, pp. 79-104.

Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.

Popovic, M.B., W. Gu and H. Herr, "Conservation of Angular Momentum in Human Movement," MIT AI Laboratory—Research Abstracts, Sep. 2002. pp. 231-232, 2002.

Pratt, G. and Williamson M., "Series elastic actuators," Proceedings on IEEE/RSJ International Conference on Intelligent Robots and Systems, Jan. 1995, Pittsburgh, PA, pp. 399-406.

Pratt, G., "Legged Robots: What's New Since Raibert," IEEE Robotics and Automation Magazine, Research Perspectives, Sep. 2000, pp. 15-19.

Pratt, G., "Low Impedance Walking Robots," Integ. and Camp. Bioi., vol. 42, Feb. 2002, pp. 174-181.

Pratt, J., et. al., "The RoboKnee: An Exoskeleton for Enhancing Strength and Endurance During Walking", IEEE Conf. on Robotics and Automation, Apr. 2004, New Orleans, LA, pp. 2430-2435.

Prochazka, A. and Yakovenko, S., "The neuromechanical tuning hypothesis," Prog Brain Res, vol. 165, Oct. 2007, pp. 255-265.

Prochazka, A., et. al., "Positive force feedback control of muscles," J. of Neuro-phys., vol. 77, Jun. 1997, pp. 3226-3236.

Prochazka, A., et. al., "Sensory control of locomotion: reflexes versus higher-level control," Adv Exp Med Bioi, vol. 508, 2002, pp. 357-367.

Raibert, M., "Legged Robots that Balance," The MIT Press, Nov. 1986, Cambridge, MA, p. 89.

Rassier, D., et. al., "Length dependence of active force production in skeletal muscle," Journal of Applied Physiology, vol. 86, Issue 5, May 1999, pp. 1455-1457.

Riener, R., et. al., "Stair ascent and descent at different inclinations," Gait Posture, vol. 15, Feb. 2002, pp. 32-44.

Reitman, et. al., Gait analysis in prosthetics: opinions, ideas and conclusions, Prosthetics and Orthotics International, 2002, 26, 50-57.

Robinson, D., "Design and an analysis of series elasticity in closed-loop actuator force control," Ph.D. Thesis, MIT, Jun. 2000, Cambridge, MA, pp. 1-123.

Robinson, D., "Series elastic actuator development for a biomimetic walking robot," Proceedings of IEEE/ASME International Conference on Advanced Intelligent Mechatronics, Sep. 1999, pp. 561-568.

Rosen, J., et al., "A myosignal-based powered exoskeleton system," IEEE Transactions on Systems, Man, and Cybernetics—Part A: Systems and Humans, vol. 31, No. 3, May 2001, pp. 210-222.

Ruina, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.

Rybak, I., et. al., "Modelling spinal circuitry involved in locomotor pattern generation: insights from deletions during fictive locomotion," J Physiol, vol. 577 (Pt 2), Dec. 2001, 617-639.

Sanderson, D., et. al., "Lower extremity kinematic and kinetic adaptations in unilateral below-knee amputees during walking," Gait and Posture, vol. 6, No. 2, Oct. 1997, pp. 126-136.

(56) References Cited

OTHER PUBLICATIONS

Sanger, T., "Human arm movements described by a low-dimensional superposition of principal component," Journal of NeuroScience, vol. 20, No. 3, Feb. 2000, pp. 1066-1072.
Saranli, U., "RHex: A simple and highly mobile hexapod robot," Int. Jour. Rob. Res., vol. 20, No. 7, Jul. 2001, pp. 616-631.
Sarrigeorgidis K. and Kyriakopoulos K., "Motion control of the N.T.U.A. robotic snamek on a planar surface," Proc. of the 1998 IEEE International Conference on Robotics and Automation, May 1998, pp. 2977-2982.
Schaal, S., "Is imitation learning the route to humanoid robots?" Trends in Cognitive Sciences, vol. 3, Jun. 1999, pp. 233-242.
Schaal, S. And Atkeson, C., "Constructive incremental learning from only local information," Neural Computation, vol. 10, No. 8, Nov. 1998, pp. 2047-2084.
Scott, S. and Winter, D., "Biomechanical model of the human foot: kinematics and kinetics during the stance phase of walking," J. Biomech., vol. 26, No. 9, Sep. 1993, 1091-1104.
Sentis, L. and 0. Khatib, "Task-Oriented Control of Humanoid Robots Through Prioritization," IEEE-RAS/RSJ International Conference on Humanoid Robots, Nov. 2004, Santa Monica, CA, pp. 1-16.
Seyfarth, A., "Swing-leg retraction: a simple control model for stable running," J. Exp. Bioi., vol. 206, Aug. 2003, pp. 2547-2555.
Seyfarth, A., et. al., "A movement criterion for running," J. of Biomech., vol. 35, May 2002, pp. 649-655.
Seyfarth, A., et. al., "Stable operation of an elastic three-segmented leg," Bioi.Cybern., vol. 84, 2001, pp. 365-382.
Simon F., et. al, "Convergent force fields organized in the frog's spinal cord," Journal of NeuroScience, vol. 13, No. 2, Feb. 1993, pp. 467-491.
Sinkjaer, T., et. al., "Major role for sensory feedback in soleus EMG activity in the stance phase of walking in man," J Physiol, vol. 523, No. 3, Mar. 2000, pp. 817-827.
Skinner, H. and Effeney D., "Gait analysis in amputees," Am J Phys Med, vol. 64, Apr. 1985, pp. 82-89.
Smidt et al., "An Automated Accelerometry System for Gait Analysis," J. Biomechanics, vol. 10, 1977, pp. 367-375.
Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.
Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.
Sugano et al., "Force Control of the Robot Finger Joint equipped with Mechanical Compliance Adjuster," Proc. of the 1992 IEEE/RSJ Int. Conf. on Intel I. Robots & Sys., Jul. 1992, pp. 2005-2013.
Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.
Sup, F., "Design and Control of a Powered Transfemoral Prosthesis," The International Journal of Robotics Research, vol. 27, No. 2, Feb. 2008, pp. 263-273.
Taga, G., "A model of the neuro-musculo-skeletal system for human locomotion," Bioi. Cybern., vol. 73, No. 2, Jul. 1995, pp. 97-111.
Takayuki "Biped Locomotion using Multiple Link Virtual Inverted Pendulum Model," Publication of Electronics Information and Systems Society, vol. 120, No. 2, Feb. 2000, 8 pages.
Thorough man, K. and R. Shadmehr, "Learning of action through adaptive combination of motor primitives," Nature, vol. 407, Oct. 2000, pp. 742-747.
Tomovic R. et al., "A Finite State Approach to the Synthesis of Bioengineering Control Systems," IEEE Transactions on Human Factors in Electronics, vol. 7, No. 2, Jun. 1966, pp. 65-69.
Tong, et al., "A Practical Gait Analysis System Using Gyroscopes," Medical Engineering & Physics, vol. 21, Mar. 1999, pp. 87-94.
Turker, K., "Electromyography: some methodological problems and issues," Physical Therapy, vol. 73, No. 10, Oct. 1993, pp. 698-710.

van den Bogert, A., "Exotendons for assistance of human locomotion," Biomedical Engineering Online, Oct. 2003, pp. 1-8.
van den Bogert, et al. "A Method for Inverse Dynamic Analysis Using Accelerometry," Journal Biomechanics, vol. 29, No. 7, 1996, pp. 949-954.
Veltink P., et al., "The Feasibility of Posture and Movement Detection by Accelerometry," D-7803-1377-1/93, IEEE, Oct. 1993, pp. 1230-1231.
Vukobratovic M. and Juricic, D., "Contributions to the synthesis of biped gait," IEEE Transactions on Biomedical Engineering, vol. BME-16, No. 1, Jan. 1969, pp. 1-6.
Vukobratovic M. and Stepanenko J., "Mathematical models of general anthropomorphic systems," Mathematical Biosciences, vol. 17, Aug. 1973, pp. 191-242.
Walsh, C., "Biomimetic Design of an Under-Actuated Leg Exoskeleton for Load-Carrying Augmentation," Masters Thesis, MIT, Feb. 2006, pp. 1-94.
Waters, RL., "Energy cost of walking amputees: the influence of level of amputation," J Bone Joint Surg., vol. 58, No. 1, Jan. 1976, pp. 42-46.
Wilkenfeld, A., "An Auto-Adaptive External Knee Prosthesis," Artificial Intelligence Laboratory, MIT, Sep. 2000, Cambridge, MA, pp. 1-3.
Wilkenfeld, A. J., "Biologically inspired auto adaptive control of a knee prosthesis," Ph.D. Thesis, Massachusetts Institute of Technology, Oct. 23, 2000.
Williamson, M., "Series Elastic Actuators," Artificial Intelligence Laboratory, MIT, Jan. 1995, Cambridge, MA, pp. 1-74.
Willemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.
Willemsen A., et al., "Real-Time Gait Assessment Utilizing a New Way of Accelerometry," Journal of Biomechanics, vol. 23, No. 8, 1990, pp. 859-863.
Williams, B., "Mode Estimation of Model-based Programs: Monitoring Systems with Complex Behavior," Proceedings of the International Joint Conference on Artificial Intelligence, Aug. 2001, Seattle, WA, pp. 1-7.
Winter, D. A, "Energy generation and absorption at the ankle and knee during fast, natural, and slow cadences," Clinical Orthopedics and Related Research, vol. 175, May 1983, pp. 147-154.
Winter, D, and Robertson D., "Joint torque and energy patterns in normal gait," Bioi. Cybem., vol. 29, May 1978, pp. 137-142.
Winter, D. and Sienko S., "Biomechanics of below-knee amputee gait," Journal of Biomechanics, vol. 21, No. 5, Aug. 1988, pp. 361-367.
Wisse, M., "Essentials of Dynamic Walking, Analysis and Design of two-legged robots," Ph.D Thesis, Technical University of Delft, 2004, pp. 1-195.
Woodward et al., "Skeletal Accelerations measured during different Exercises," Proceedings of the Institution of Mechanical Engineers, Part H: Journal of Engineering in Medicine, vol. 207, Jun. 1993, pp. 79-85.
Wu, The Study of Kinematic Transients in Locomotion Using the Integrated Kinematic Sensor, IEEE Transactions on Rehabilitation Engineering, vol. 4, No. 3, Sep. 1996, p. 193-200.
Yakovenko, S., et. al., "Contribution of stretch reflexes to locomotor control: a modeling study," Bioi Cybern, vol. 90, No. 2, Jan. 2004, pp. 146-155.
Yun X., "Dynamic state feedback control of constrained robot manipulators," Proc. of the 27th conference on Decision and Control, Dec. 1988, pp. 622-626.
Zlatnik, D., et. al., "Finite-state control of a trans-femoral prosthesis," IEEE Trans. on Control System Technology, vol. 10, No. 3, May 2002, pp. 408-420.
U.S. Appl. No. 13/359,216, Controlling Powered Human Augmentation Devices, filed Jan. 12, 2012.
U.S. Appl. No. 13/356,230, Terrain Adaptive Powered Joint Orthosis, filed Jan. 23, 2012.
U.S. Appl. No. 13/417,949, Biomimetic Joint Acuators, filed Mar. 12, 2012.

(56) References Cited

OTHER PUBLICATIONS

Blaya, J.A. et al., "Adaptive Control of a Variable-Impedance Ankle-Foot Orthosis to Assist Drop Foot Gait", Artificial Intelligence Lab and Harvard-MIT Division of Health Sciences and Technology, Boston, MA, 30 pages (2004).

Blaya, J.A. et al., "Active Ankle Foot Orthoses (AAFO)", http://www.ai.mit.edu, Artificial Intelligence Laboratory, Massachusetts Institute of Technology, Cambridge, MA, 3 pages (2001).

Drake, C., "Foot & Ankle Splints or Orthoses", HemiHelp Information Sheet, London, United Kingdom, 3 pages, www.hemihelp.org.uk/leaflets/hbleaflets90.htm: Retrieved on Jun. 20, 2003.

Klute, et al., "Variable Stiffness Prosthesis for Transtibial Amputees", Dept. of Veteran Affairs, Seattle, WA, USA, 2 pages (2003).

Light, et. al., "Skeletal Transients on Heel Strike in Normal Walking with Different Footwear", J. Biomechanics, vol. 10, pp. 477-480 (1980).

\* cited by examiner

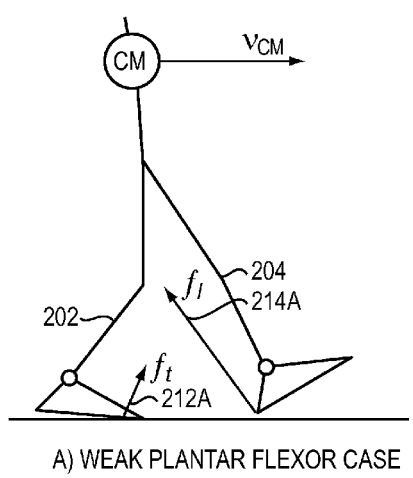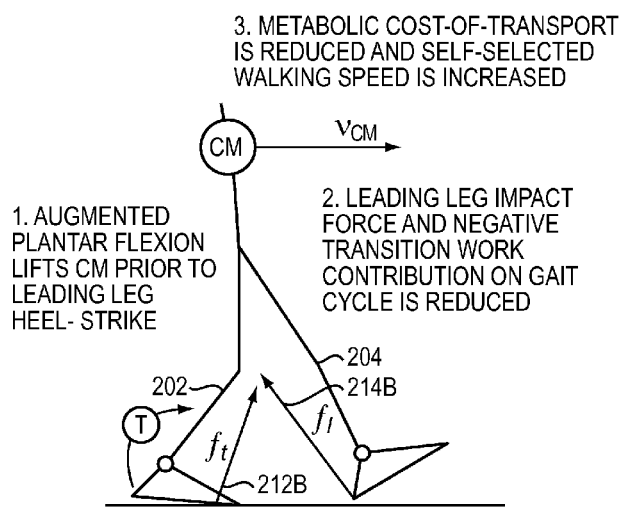
A) WEAK PLANTAR FLEXOR CASE
FIG. 2A
B) AUGMENTED PLANTAR FLEXOR
FIG. 2B

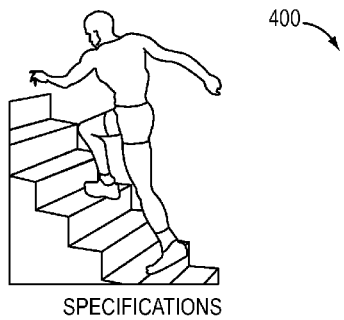

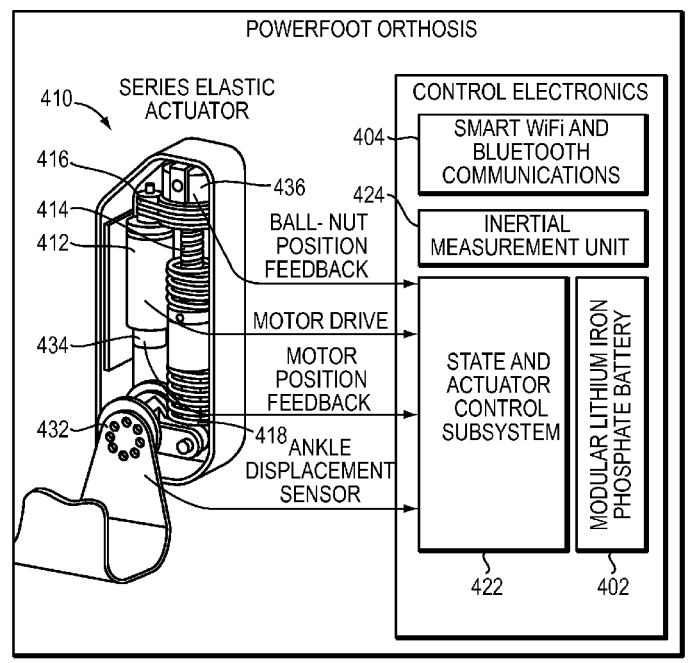

SPECIFICATIONS
- WEARER WEIGHT RANGE: 45-110 kg
- WEARER ATTACHMENT: CUSTOM 3-D PRINTED BONDED Ti/SOFT ELASTOMER
- L 1 DESIGN LIFE: 5 MILLION CYCLES (5 YEARS)
- ORTHOSIS MASS (WEIGHT): 1.2 kg ( 2.6Lbs)
- BATTERY STORAGE: 2000 STEPS FOR 70 kg WEARER
- ACTUATOR
  - PEAK TORQUE: 1.7 N-m/kg
  - PEAK POWER: 5W/kg
  - ANKLE ANGLE RANGE: -22° TO +6°
- CLINICIAN CONFIGURABILITY: BLUETOOTH/ ANDROID GRAPHICAL INTERFACE
- RESEARCH: REAL-TIME, WiFi DATA ACQUISITION: (50 STATE VARIABLES AT 500 HZ)

FIG. 4A

POWERED JOINT ORTHOSIS

RELATED APPLICATIONS

This application claims priority to and benefit of U.S. Provisional Patent Application Ser. No. 61/431,277, filed on Jan. 10, 2011, the entire content of which is hereby incorporated by reference in its entirety.

FIELD OF THE INVENTION

This invention relates generally to lower-extremity orthotic apparatus designed to emulate human biomechanics and to normalize function, components thereof, and methods for controlling the same.

BACKGROUND

Approximately 65% of service members seriously injured in Iraq and Afghanistan sustain injuries to their extremities. Many of these individuals experience muscle tissue loss and/or nerve injury, resulting in the loss of limb function or substantial reduction thereof. Injuries to the lower leg can be particularly devastating due to the critical importance of the ankle in providing support for body position, and in propelling the body forward economically during common functions such as level-ground walking and the ascent and descent of stairs and slopes.

Increasingly, robotic technology is employed in the treatment of individuals suffering from physical disability, either for the advancement of therapy tools or as permanent assistive devices. An important class of robotic devices provides therapy to the arms of stroke patients. Additionally, lower-extremity robotic devices have been developed for the enhancement of locomotor function. Although decades of research has been conducted in the area of active permanent assistive devices for the treatment of lower-extremity pathology, there devices are not designed to produce a biomimetic response, generally described in terms of joint torque, joint angle, and other related parameters as observed in a human not having substantial muscle tissue injury and not using any device to assist in ambulation. Therefore, the robotic devices usually result in unnatural ambulation and may even cause significant discomfort to the wearer. As such, many commercially available ankle-foot orthoses remain passive and non-adaptive to the wearer even today.

These passive devices cannot adequately address two major complications of anterior muscle weakness, which include slapping of the foot after heel strike (foot slap) and dragging of the toe during swing (toe drag). At heel strike, the foot generally falls uncontrolled to the ground, producing a distinctive slapping noise (foot slap). During midswing, toe drag prevents proper limb advancement and increases the risk of tripping. A conventional approach to the treatment of anterior/posterior compartment leg weakness is a mechanical brace called an Ankle Foot Orthosis (AFO). Although AFOs may offer some biomechanical benefits, disadvantages still remain. W. E. Carlson, C. L. Vaughar, D. L. Damiano, and M. F. Abel, "Orthotic Management of Gait in Spastic Diplegia," *American Journal of Physical Medicine & Rehabilitation*, vol. 76, pp. 219-225, 1997, found that AFOs did not improve gait velocity or stride length in children with cerebral palsy. Still further, J. F. Lehmann, S. M. Condon, B. J. de Lateur, and R. Price, "Gait Abnormalities in Peroneal Nerve Paralysis and Their Corrections by Orthoses: A Biomechanical Study," *Archives of Physical Medicine and Rehabilitation*, vol. 67, pp. 380-386, 1986 June, discovered that although a constant stiffness AFO was able to provide safe toe clearance in drop-foot patients, the device did not reduce the occurrence of slap foot.

Moreover, the passive devices typically do not address a dominant complication of posterior muscle weakness i.e., the lack of late stance powered plantar flexion. Since terminal stance powered plantar flexion is paramount for limiting heel strike losses of the adjacent leg, a patient with weak posterior muscles will likely experience an increase in impact force on the leading leg at heel strike and, consequently, an increase in the metabolic rate of walking. Therefore, there is a need for improved systems and methods of permanent assistive devices for the treatment of lower-extremity pathology.

SUMMARY

In various embodiments, the present invention provides devices and methods for operating/controlling such devices so as to assist patients with anterior and/or posterior compartment leg weakness by eliminating or significantly reducing foot slap and/or foot drop. This is achieved, using a type of device called a PowerFoot Orthosis (PFO); the PFO devices are capable of position, impedance, and non-conservative torque control in both dorsiflexion and plantar flexion directions in accordance with the gait-cycle, terrain (e.g., ground slope and stairs) and walking speed. The PFOs can also augment ankle torque during stance so as to perform the net non-conservative work and to deliver the mechanical power necessary to normalize the augmented ankle mechanics. Thus, the PFO devices can provide at least a biomimetic response and optionally can be used to augment normal biomechanical response. Offering control enhancement for both stance and swing phases, the PFO can be used as a permanent assistive device where actuation, sensing, power, and computation are all packaged within a small, lightweight, autonomous, manufacturable, and high cycle-life package that can readily fit beneath a normal pant leg.

In a laboratory study, a tethered powered ankle-foot orthosis was shown to reduce both foot slap and toe drag in patients with anterior muscle weakness. The PFO can help facilitate the return to physiological function of soldiers or civilians who have experienced incapacitating injuries to their anterior and/or posterior compartment leg musculature, limiting their capacity to walk. In addition to the potential for improved walking speed and ambulation economy, decreased demand on the leading limb in walking may reduce long-term morbidity and promote rapid return to physiological function. The PFO can also assist humans having uninjured anterior and/or posterior compartment leg musculature in activities such as carrying a heavy load over a long distance to enhance their strength and endurance.

In one aspect, embodiments of the invention feature a powered device for augmenting a joint function of a human during a gait cycle. The device includes a powered actuator for supplying an augmentation torque and/or an impedance to a joint, and a controller to modulate the augmentation torque, the impedance, and a joint equilibrium according to a phase of the gait cycle to provide at least a biomimetic response. The controller may be configured to modulate, within the gait cycle, the augmentation torque, the impedance, and the joint equilibrium according to a speed of ambulation, e.g., walking speed, and/or terrain. The powered actuator may include a series-elastic actuator, and the series-elastic actuator may include a transverse-flux motor.

In some embodiments, the device may also include a first sensor to generate a first sensor signal related to terrain and/or speed of ambulation, and the controller may be adapted to kinematically reconstruct a path of the joint within the gait cycle according to the first sensor signal. The device may also include an accelerometer to determine heel strike. The kinematic reconstruction may include computing a pose and an origin of a co-ordinate frame associated with a link connected to the joint and/or another joint proximal to the joint.

In some embodiments, computing the pose includes creating a homogeneous transformation of the co-ordinate frame, and the homogeneous transformation may include a 3×1 vector defining an origin of the co-ordinate frame and a 3×3 matrix comprising unit vectors of the co-ordinate frame. At least one point within the co-ordinate frame may correspond to a link connected to the joint and/or another joint proximal to the joint. In some embodiments, the joint is an ankle joint and a point that corresponds to the link may be a distal end (e.g., the knee joint) and/or a proximal end (e.g., the ankle joint) of a tibia connected to the ankle.

In some embodiments, the controller is adapted to determine a terrain type as one of substantially level surface, sloping surface, and stairs, and the controller may also be adapted to determine an activity according to the terrain type. The activity can be one of ascending stairs, descending stairs, walking on a substantially level surface, walking on a surface sloping up, and walking on a surface sloping down. The device may include a second sensor to provide a second sensor signal related to one or more of a pitch angle, a pitch velocity, an ankle angle, and joint torque, and the controller may be adapted to determine the phase of the gait cycle based at least in part on the second sensor signal.

In some embodiments, the powered actuator includes a motor, and the device further includes a third sensor configured to provide a third sensor signal related to a velocity of the motor. The device may also include a timer to provide a timing signal to the controller, and the controller may be adapted to determine the phase of the gate cycle based at least in part on the timing signal. The joint equilibrium may vary in time during the gait cycle, and the modulation may include modeling the joint equilibrium as a second-order response to a joint-position goal to be achieved prior to a next phase of the gait cycle. The modulation may also include adjusting at least the augmentation torque such that the modeled joint equilibrium is approximately equal to a pre-determined joint equilibrium. The second-order response can be an over-damped response. In some embodiments, a biomimetic response is achieved within the gait cycle. The device may also include a parallel and/or series elastic element for applying a torque to the joint, thereby dorsiflexing the joint. The joint may be an ankle joint.

In some embodiments, the controller is adapted to modulate the augmentation torque according to a positive-force feedback. The augmentation torque may be modulated according to the positive-force feedback in combination with a natural joint torque supplied by the human, such that the combined torque approximates a normal joint torque. The positive-force feedback may be adjusted according to terrain and/or ambulation speed.

In some embodiments, the controller is adapted to modulate the augmentation torque according to scaling factor. The controller may also be adapted to attenuate the augmentation torque according to a protocol. The device may include an external signal to stimulate the actuator. The impedance may be a linear impedance or a non-linear impedance.

In another aspect, embodiments of the invention feature a powered method for augmenting a joint function of a human during a gait cycle. The method includes supplying at least one of an augmentation torque and an impedance to a joint. The method also includes modulating the augmentation torque, the impedance, and a joint equilibrium according to a phase of the gait cycle to provide at least a biomimetic response.

The impedance may include a stiffness component, a damping component, and/or an inertial component. Modulating the impedance may include determining the stiffness component and/or the damping component. In some embodiments, the impedance includes a non-linear impedance, and modulating the impedance may include determining a gain of the non-linear impedance and an exponent of the non-linear impedance.

The phase of the gait cycle may be determined, at least in part, according to a sign of joint angular velocity, joint angular velocity, joint inertial rate, joint acceleration, and/or joint torque. The augmentation torque may be supplied in addition to natural joint torque supplied by the human to achieve a pre-determined total joint torque response. In some embodiments, modulating includes or consists essentially of applying a closed-loop torque control at the joint. The method may also include modeling the joint torque, and determining the phase of the gait cycle based on the joint torque model.

In some embodiments, the method further includes kinematically reconstructing a path of a proximal link connected to the joint and/or another joint proximal to the joint within the gait cycle. The kinematic reconstruction may include determining a terrain type as one of a substantially level surface, a sloping surface, and stairs. The kinematic reconstruction may also include determining an activity according to the terrain type. The activity can be one of ascending stairs, descending stairs, walking on substantially level surface, walking on a surface sloping up, and walking on a surface sloping down.

In some embodiments, the impedance is supplied to the joint during a controlled plantar flexion phase of the gait cycle in order to mitigate foot slap. The augmentation torque, the impedance, and the joint equilibrium may be modulated in order to mitigate foot drop and/or to provide a pre-determined net work according to ambulation speed, terrain, or both.

In some embodiments, the augmentation torque is modulated according to a positive-force feedback. The augmentation torque may be modulated according to the positive-force feedback in combination with a natural joint torque supplied by the human such that the combined torque approximates at least a normal joint torque. The positive-force feedback may include a gain and an exponent, and the gain and/or the exponent may be determined according to a speed of ambulation, terrain or both.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means±10% and, in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2a schematically illustrates human ankle behavior in a weak plantar flexor case;

FIG. 2b schematically illustrates human ankle behavior in an augmented plantar flexor case, according to one embodiment;

FIGS. 4a and 4b illustrate two PFO devices according to two different embodiments;

DESCRIPTION

Figure 1:
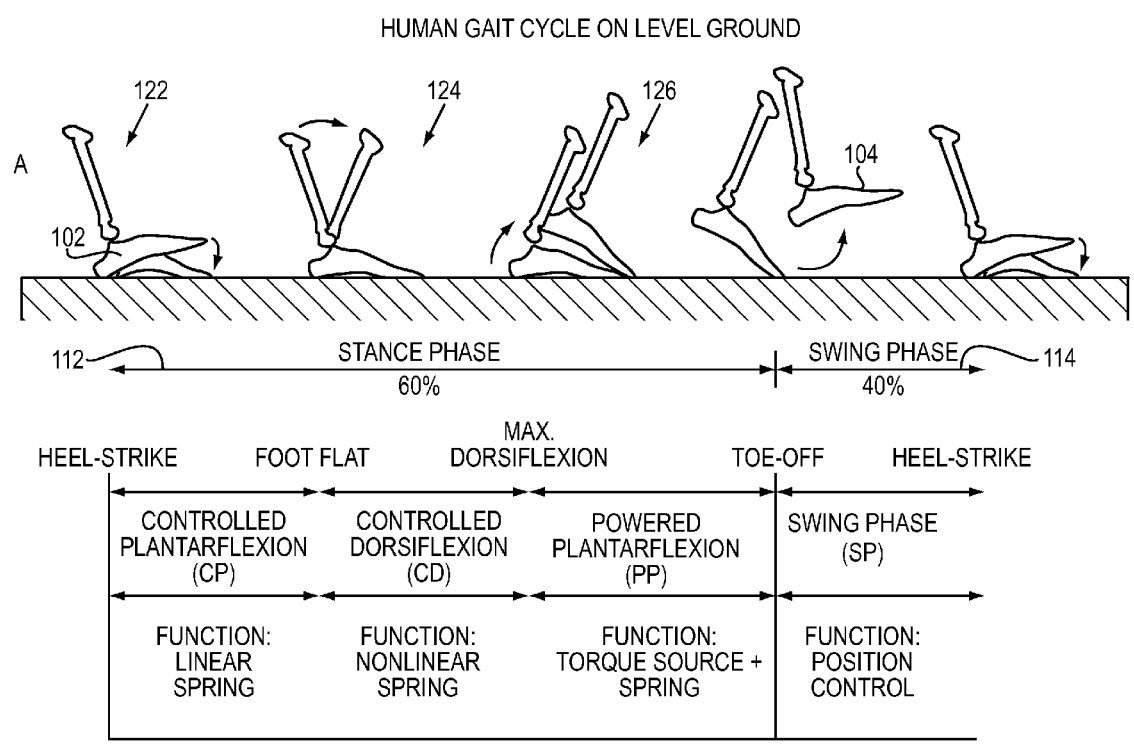
FIG. 1 depicts various phases of a human gait cycle.

The entire contents of each of U.S. patent application Ser. No. 12/157,727 "Powered Ankle-Foot Prosthesis" filed on Jun. 12, 2008 (Publication No. US2011/0257764 A1) and U.S. patent application Ser. No. 12/552,013 "Hybrid Terrain-Adaptive Lower-Extremity Systems" filed on Sep. 1, 2009 (Publication No. US2010/0179668 A1) are incorporated herein by reference. FIG. 1 illustrates normal ankle function in each of the four phases of a human gait cycle during level-ground ambulation. In the controlled plantar flexion state (CP) 122 during the stance phase 112, the ankle 102 serves as a linear spring impedance that cushions the foot-strike impact in accordance with the gait speed. In the controlled dorsiflexion state (CD) 124 during stance 112, the ankle 102 behaves as a non-linear spring that stores energy for later release in the powered plantar flexion state (PP) 126. In PP 126, the ankle 102 delivers a reflex response—an uncontrolled release of torque that both lifts and propels the wearer in accordance with gait speed. In the swing phase 114, the ankle 102 applies position control to first reposition the foot 104 after toe-off to achieve ground clearance and then to prepare the foot 104 for the foot strike initiation in the next gait cycle. The repositioning for toe-off and heel strike is generally accomplished through modulation of impedance and joint equilibrium so as to achieve, in the augmented system, the mass-spring-damper dynamics of the human ankle. In the swing phase, the repositioning and heel strike preparation is accomplished through modulation of the impedance and joint equilibrium to model human ankle spring-mass-damper dynamics for the augmented system.

Platform and PFO (described with reference to FIGS. 4a and 4b below) mimic human ankle behavior during the gait cycle—modulating impedance, torque and joint equilibrium in accordance with the gait cycle and speed and, optionally, terrain—and augments the ankle torque of the wearer, employing positive force feedback to mimic the calf muscle-Achilles tendon reflex response, thereby normalizing the ankle response as described below. A time-varying joint equilibrium (e.g., position and/or angle) in conjunction with an impedance (stiffness and damping) mimics the biomechanics. Therefore, a powered biomimetic orthosis (e.g., a PFO)—when worn by a wearer with posterior and/or anterior weakness—may deliver measurable benefits through reduction of leading leg impact force, reduction in metabolic cost-of-transport and increased walking speed.

With reference to FIG. 2a, if a wearer exhibits posterior weakness, the trailing leg 202 typically delivers reduced lifting force 212a at the time that the foot on the leading leg 204 strikes the ground. This deficiency in turn can increase the impact force 214a on the leading leg 204 and the "negative work" contribution during the weight transfer (transition) from the trailing to the leading leg. The body may attempt to adapt by applying additional "transition work" to counteract this negative work contribution, thereby increasing metabolism and reducing the self-selected walking speed. FIG. 2b illustrates that using biologically-inspired Platforms according to the invention, ankle torque is augmented during PP 126, thereby lifting the wearer's center-of-gravity at approximately the time of leading leg 204 impact, thereby reducing the impact force 214b and the negative work contribution. Consequent transition work reduction leads to reduced metabolic cost and an increased self-selected walking speed.

Figure 3:
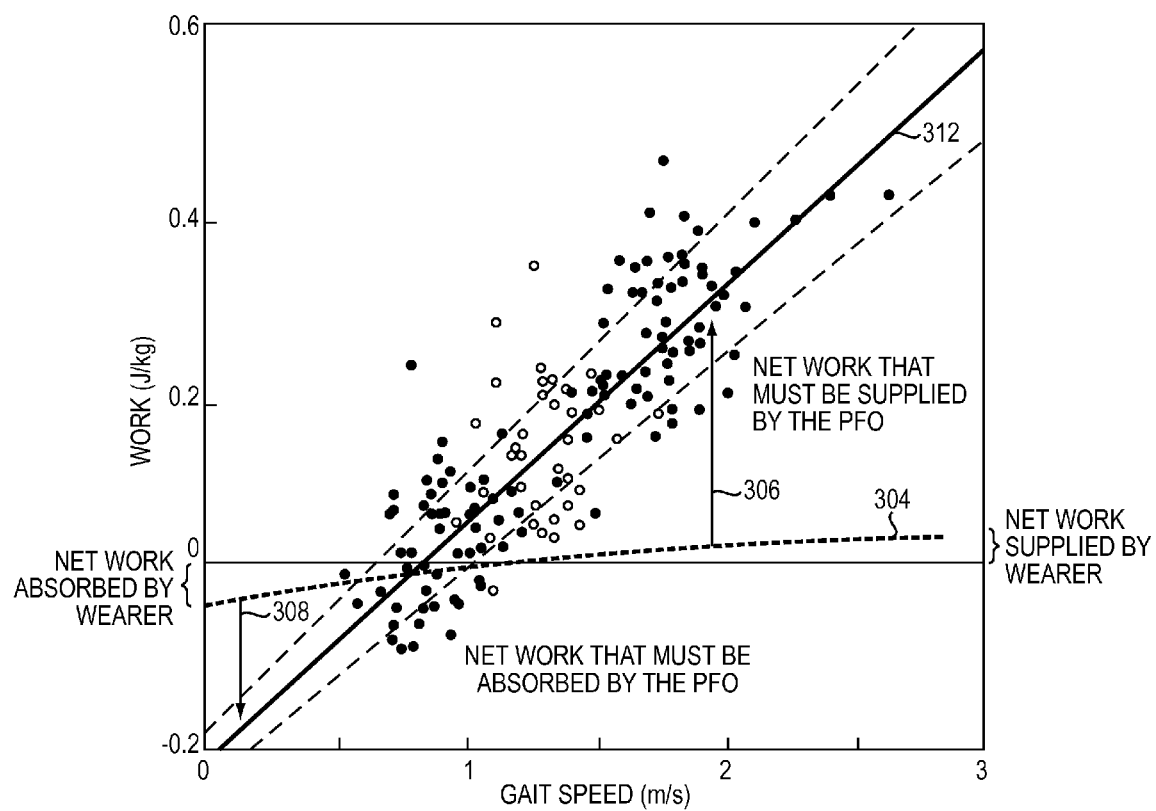
FIG. 3 shows the normalized work performed by a typical ankle during a gait cycle at different walking speeds.

FIG. 3 illustrates that in an intact ankle population, the normalized work performed by the ankle during a gait cycle varies generally linearly with gait speed, as shown by line 302. The dashed line 304 illustrates the deficiency implied by bilateral weakness. As shown by vectors 306, 308, the Platform must perform both positive and negative work to make up for the deficiencies and achieve a biomimetic response. Such work generally varies with gait speed.

Figure 5:
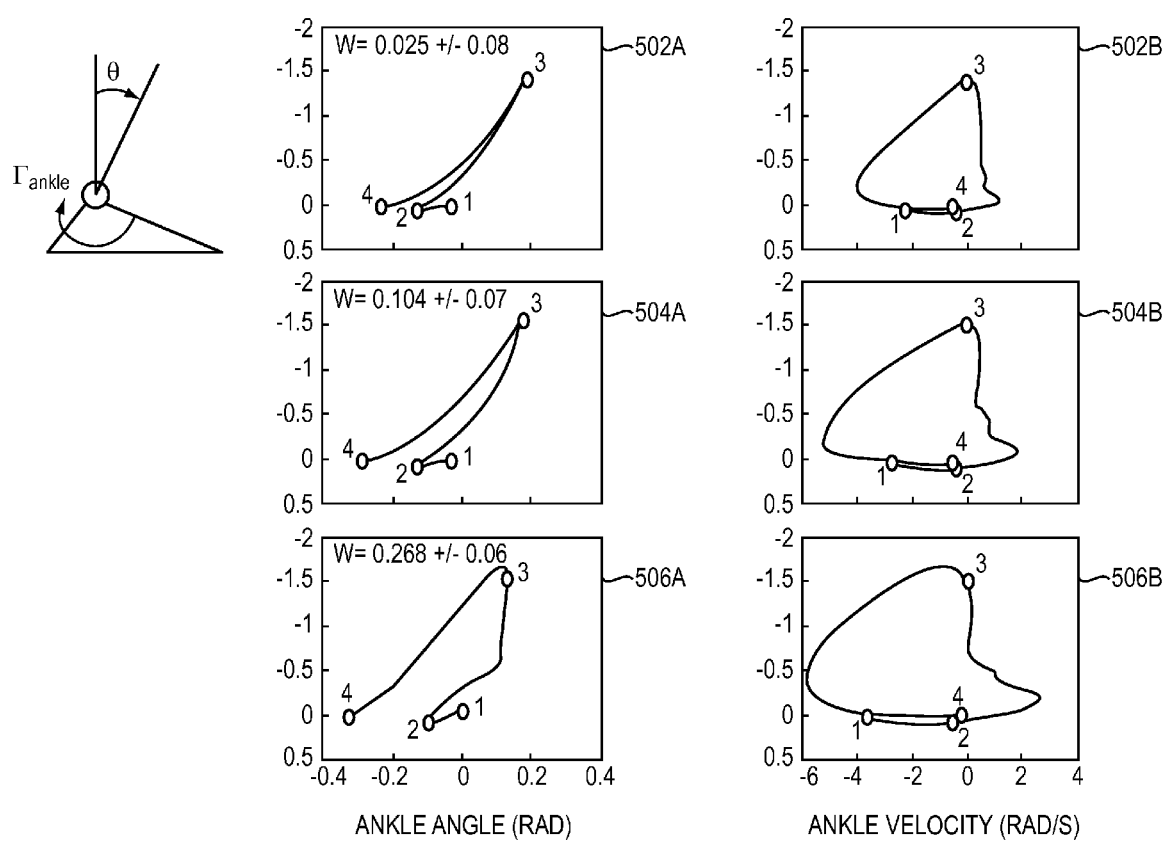
FIG. 5 depicts a relationship between ankle torque, ankle angle, and ankle-angle velocity for a typical ankle at different walking speeds.
Figure 6:
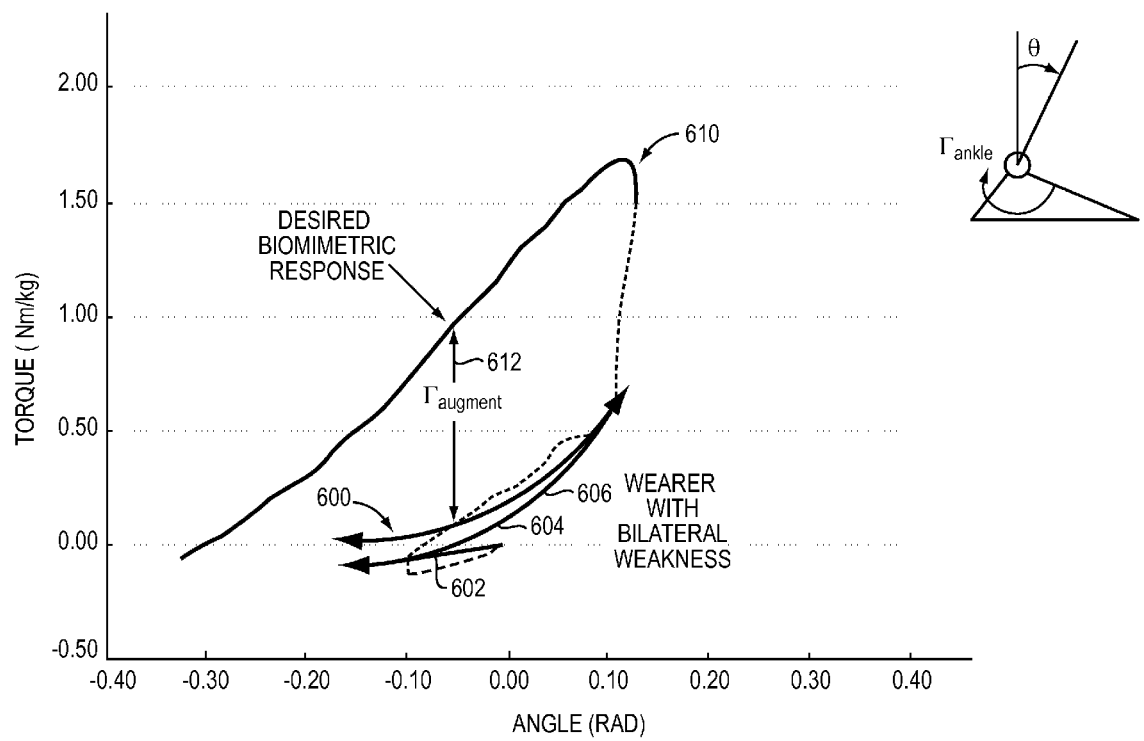
FIG. 6 depicts a augmentation of ankle torque according to one embodiment.

FIG. 4a schematically depicts the specifications and illustrates the actuator and control architecture employed to achieve them according to one embodiment of the invention. The Platform 400 is designed to be adapted to the full range of military and civilian personnel through use of a quiet, light-weight and rugged actuator 410. A modular battery 402 with a 2000 step capacity (wearer weighing 70 kg with bilateral deficiency) is employed. It is anticipated that a typical wearer will need to replace this lightweight battery pack between one and two times per day. The actuator 410 is designed so as to deliver at least a full biomimetic torque and angle response to cover a gait speed range from 0-1.75 m/sec. as discussed and shown in FIG. 5. Finally, the Platform 400 employs two embedded wireless interfaces 404. The Bluetooth interface serves as a pathway for PDA-based tuning by clinicians and researchers to normalize the torque response—specifically to program the Platform to deliver $\Gamma_{augment}$ (described below with reference to FIG. 8) as required in each phase of the gait cycle as shown in FIG. 6. The smart WiFi interface serves as a pathway for researchers to acquire control state variables and sensory feedback from the Platform 400 and to synchronize this telemetry with external biomechanical instrumentation.

As depicted in FIG. 4a, the Platform 400 employs a series-elastic actuator (SEA) 410 to drive the powered orthosis. See, for example, U.S. Pat. No. 5,650,704 "Elastic Actuator for Precise Force Control" the disclosure of which is incorporated herein by reference. As shown, a multi-processor control system (State and Actuator Controller) 422 uses feedback from the SEA 410 to deliver the appropriate response in accordance with the phase of the gait cycle and the walking speed and, optionally, according to the terrain and the wearer's activity thereon (e.g., walking upslope or downslope, ascending or descending stairs, etc.). A three-phase brushless motor driver (Motor Driver) 412 interfaces to the State and Actuator Controller 422 to accomplish closed-loop torque control of the SEA 410. An Inertial Measurement Unit (IMU) 424, employing a three-axis rate gyro and a three-axis accelerometer, provides feedback to sense state transitions within the gait cycle, to measure gait speed and to discriminate terrain modality. Terrain modality may refer to the type of the terrain such as level and/or sloping ground and stairs and, as such, discrimination of terrain modality may include determining a transition between different terrain types. A WiFi/Bluetooth communication module 404 is employed to interface directly to the State Controller and Actuator Controller 422 to facilitate research data acquisition and PDA-based clinician tuning.

The SEA 410 employs a robust ball-nut and ball-screw mechanism 414 driven by the high-rpm brushless motor 412 through a redundant aramid fiber twin belt transmission 416 to achieve about L1 design life of over five million cycles (i.e., a design whereby 99% of a population survive longer than the reported design life with 95% statistical confidence). The ball-nut 414 of the SEA 410 drives the foot support crank-arm mechanism through a bilateral spring assembly 418 exhibiting a weak stiffness in plantar flexion and a stiffer spring in dorsiflexion. In this application, the bilateral spring 418 is used 1) to store energy in controlled dorsiflexion for later release in the reflex response delivered in powered plantar flexion and 2) to serve as a sensing means for achieving closed-loop torque control of the actuator 410. By accomplishing the former, the peak power of the motor 412, and hence motor size and weight, may be reduced by over 40% compared to an actuator without the spring storage. In the latter, spring 418 displacement is used to estimate and thereby control drive torque in a way that attenuates the effect of friction—enabling a backdrivable means of actuation that mimics biology. Ankle angle sensor 432, motor position sensor 434, and ball-screw position sensor 436 embedded in the actuator 410 are employed to sense the state of the actuator 410 and to provide a basis for controlling the brushless motor 412 and for modulation of the PFO impedance, torque and position in accordance with the phase of the gait cycle and gait speed.

Figure 4B:
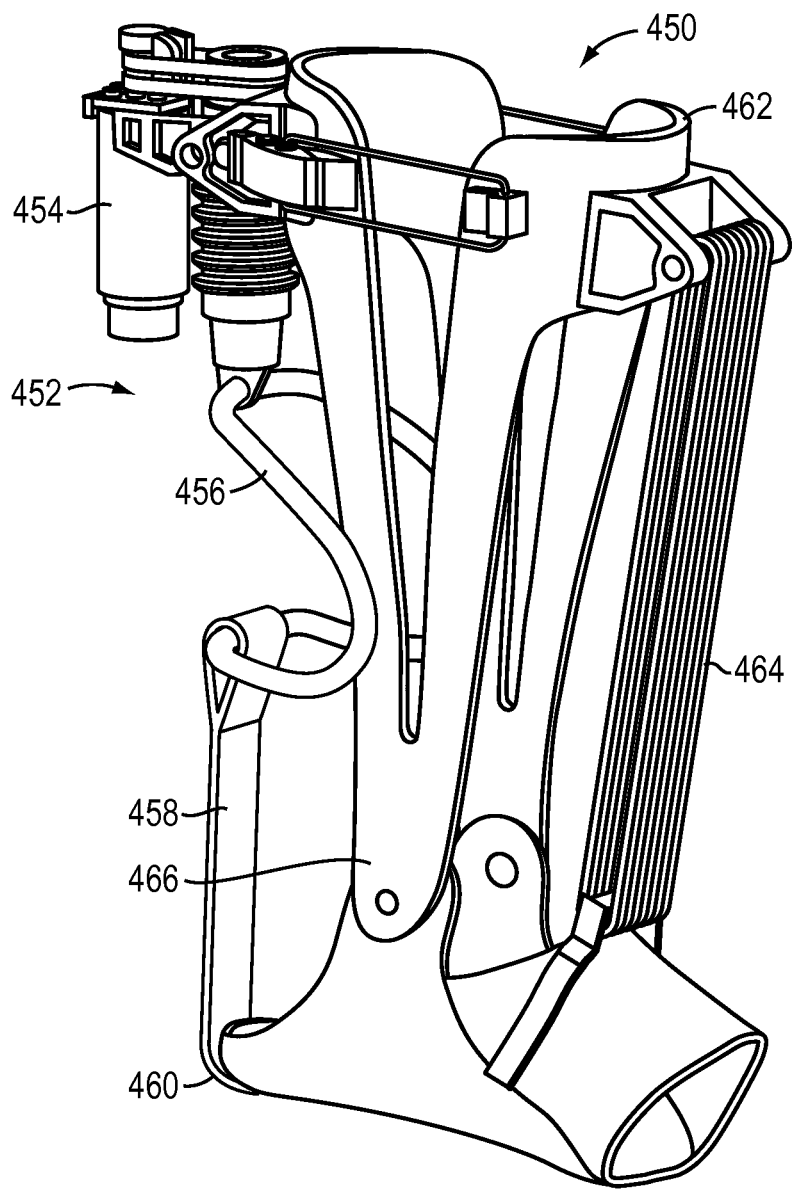

Another PFO device 450 shown in FIG. 4b includes a SEA 452 which includes a motor 454, redundant belt drive and ball nut/screw transmission and an elastic element 456 in series. The motor 454 can be a transverse-flux or other efficient, high-torque motor, optionally eliminating the belt drive for a direct drive system. The elastic element 456 is in communication with a stiff element 458, which is coupled to an elastomer foot support 460. A cuff 462 that may be adapted for a comfortable fit to a lower-leg portion of a wearer is coupled to the SEA 452. A controller circuitry for controlling the SEA 452 may be mounted on a housing of the SEA 452 and an inertial measurement unit may be mounted on the cuff 462. A parallel elastic element 464 is coupled to the cuff 462 and the elastomer 460 anterior of the ankle pivot joint 466, in opposition to the SEA 452 and element 458 disposed posterior of the joint 466.

A biomimetic response can be described in terms of various parameters such as joint torque, joint power, joint angle, etc., and other related parameters such as net work. These parameters generally vary with walking speed. Therefore, relationships between joint power and walking speed, net work and walking speed, etc., individually or in combination, generally provide a projection of a biomimetic response. In FIG. 5, chart 502a depicts representative ankle torque and ankle angle, and chart 502b depicts representative ankle torque and ankle-angle velocity of a typical ankle at a walking speed of about 0.75 m/sec. Similarly, charts 504a, 504b depict representative ankle torque and ankle angle, and ankle torque and ankle-angle velocity, respectively, of a typical ankle at a walking speed of about 1.25 m/sec. Charts 506a, 506b depict representative ankle torque and ankle angle, and ankle torque and ankle-angle velocity, respectively, of a typical ankle at a walking speed of about 1.75 m/sec. In each of these charts, a transition from data-point 1 to data-point 2 corresponds to the CP state, a transition from data-point 2 to data-point 3 corresponds to the CD state, a transition from data-point 3 to data-point 4 corresponds to the PP state, and a transition from data-point 4 back to data-point 1 corresponds to the swing phase.

With reference to FIG. 6, the portion 602 of the ankle-torque with respect to ankle-angle curve 600 corresponds to the CP phase of a wearer whose joint (e.g., ankle, knee, etc.) function is diminished so as to exhibit bilateral weakness. The portion 604 corresponds to the CD phase of the curve 600, and the portion 606 corresponds to the PP phase of the curve 600. A desired biomimetic response is depicted by the curve 610. In order to achieve such a response, an augmentation torque, $\Gamma_{augment}$ 612 may be supplied to the joint (e.g., ankle, knee, etc.). The Platform 400 and/or the PFO 450 described above can be controlled as described below with reference to FIGS. 7 and 8, so as to provide the augmentation torque $\Gamma_{augment}$ 612 such that a desired biomimetic response 610 according to the wearer's walking speed (e.g., as shown in FIG. 5) can be achieved.

Figure 7:
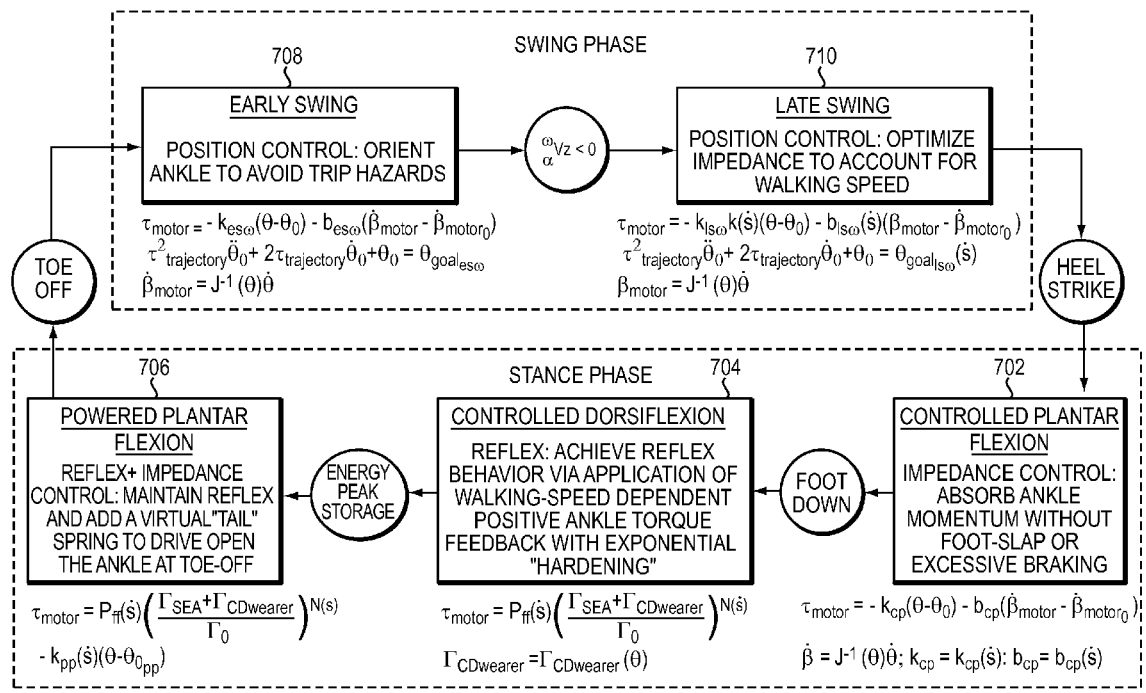
FIG. 7 schematically illustrates various states of a controller for controlling a PFO device according to one embodiment.

With reference to FIG. 7, the biologically-inspired state machine 700 that substantially implements various joint functionalities described with reference to FIG. 1 includes a Controlled Plantar Flexion State 702. The Platform 400 or PFO 450 applies a linear spring and damping impedance in accordance with the walking speed based on:

$$\tau_{motor} = -k_{cp}(\theta-\theta_0) - b_{cp}(\dot{\beta}_{motor}-\dot{\beta}_{motor_0})$$

$$\dot{\beta} = J^{-1}(\theta)\dot{\theta}; k_{cp} = k_{cp}(\dot{s}); b_{cp} = b_{cp}(\dot{s})$$

where $\tau_{motor}$ is the commanded SEA motor torque;

$\theta$ is the ankle angle;

$\beta_{motor}$ is the motor angle corresponding to the ankle angle;

$\dot{s}$ is the estimated gait speed at foot-strike estimated by the IMU; and

J is the Jacobian that relates motor speed, $d\beta/dt$ to $d\theta/dt$ as above assuming no spring deflection. The Jacobian captures the non-linear relationship arising from the actuator-joint linkage kinematics.

The mass of the motor 454 can provide an inertial component in addition to the linear spring and/or damping components.

Transition into this state 702 is accomplished by sensing by the IMU 424 the distinctive vibration that typically occurs when the foot strikes the ground. The impedance of the joint may be configured and scaled so as to prevent foot slap in accordance with walking speed and the response needed to normalize the augmented response of the wearer.

Transition into the Controlled Dorsiflexion State 704 is accomplished when the ankle angle velocity detected by the IMU 424 and/or the ankle sensor 432 switches positive, typically when the foot-flat condition is achieved. In this state 704, a reflex response is achieved through non-linear positive feedback, as defined in the relation:

$$\tau_{motor} = P_{ff}(\dot{s})\left(\frac{\Gamma_{SEA} + \Gamma_{CDwearer}}{\Gamma_0}\right)^{N(\dot{s})}$$

$$\Gamma_{CD_{wearer}} = \Gamma_{CD_{wearer}}(\theta)$$

In this, the reflex/positive-feedback gain $P_{ff}(\dot{s})$ and the exponent (non-linear spring) $N(\dot{s})$ are both functions of the estimated gait speed at foot-flat. $\Gamma_0$ is a normalizing torque comparable to the maximum torque in dorsiflexion at the self-selected walking speed. $\Gamma_{SEA}$ is the torque in the series spring. A "hard stop" spring model, $\Gamma_{CD_{wearer}}(\theta)$, is used to model the wearer torque response at extremes of dorsiflexion ($\theta > 0$) so that at least a biomimetic response can be achieved. In the equations above, functions of velocity can, by those proficient in the art, be extended to include terrain activity, including slope and stair. Generally, ascent of slope and stair will require higher positive force feedback gain and lower exponent. Descent of slope and stair will generally require lower gain and higher exponent. Ascent of slopes will generally require lower CP stiffness while descent of slopes will generally require higher damping.

Transition into the Powered Plantar Flexion State 706 is accomplished when the ankle angle velocity switches negative. The reflex response is augmented by a "tail spring" (e.g., elastic element 456) to drive full plantar flexion of the ankle per the relation:

$$\tau_{motor} = P_{ff}(\dot{s})\left(\frac{\Gamma_{SEA} + \Gamma_{CDwearer}}{\Gamma_0}\right)^{N(\dot{s})} - k_{pp}(\dot{s})(\theta - \theta_{0_{pp}})$$

where $\theta_{0_{pp}}$ is the desired equilibrium state of the ankle in plantar flexion.

$P_{ff}(\dot{s})$, $k_{pp}$, and $k_{cd}$ can be functions of terrain modality, as described above to reduce the net non-conservative work when going downslope, descending stairs, etc. and to increase the net non-conservative work when going upslope, ascending stairs, etc.

Transition into Early Swing State 708 occurs when the detected SEA 410 torque, $F_{SEA}$, approaches a programmable percentage of peak torque, generally a small percentage of the peak torque indicating that the toe is off or nearly off the ground. In this state 708, position control (impedance control with an over-damped joint equilibrium trajectory) is employed to achieve proper ground clearance through use of an organically-derived trajectory, $\theta_0(t)$ that smoothly transitions to a goal position, $\theta_{goal} = 0$ to simulate an overdamped inertia-spring-damper mechanical response.

Transition into Late Swing State 710 occurs when the IMU 424 detects a negative, vertical Cartesian (world-frame referenced) velocity, $^WV_z$. In this state, position control is again used but with a smooth trajectory that converges to a time-varying goal point, $\theta_{goal}$, that is a function of gait speed and terrain slope, each estimated by the IMU 424. The impedance (stiffness and damping) applied to position and velocity errors referenced to the trajectory (equilibrium) $\theta_0(t)$ is set in accordance with gait speed and terrain angle. In the case of stair descent, the equilibrium angle may be set to a plantar flexed position and impedance can be heavily damped impedance to absorb energy in toe-strike.

Figure 8:
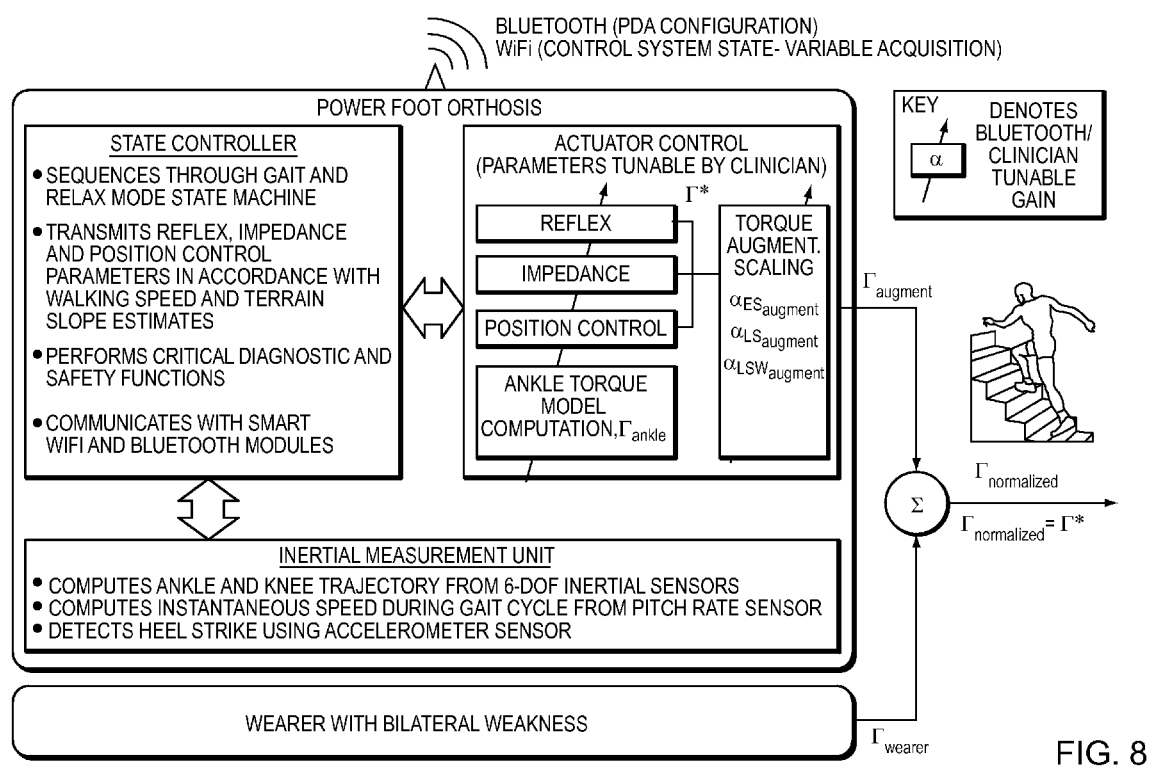
FIG. 8 schematically illustrates operation of the controller of FIG. 7 according to one embodiment.

FIG. 8 illustrates how the Platform 400 or PFO 450 can augment the torque of the wearer to achieve a normalized biomimetic response. In other embodiments, the Platform 400 or PFO 450 can augment the torque of the wearer to achieve a response that can enable a wearer who does not have a diminished natural joint function to perform activities such as walking or running a long distance, carrying a heavy load, etc. The state machine 700 modulates the SEA 410 impedance, reflex and position control response in accordance with gait speed and terrain modality inputs from the IMU 424. The SEA control internally computes the normalized biomimetic torque, $\Gamma^*$, in each state of the gait cycle. State-specific attenuation, set initially by the clinician, then scales $\Gamma^*$ and drives the SEA 410 to deliver just the right torque, $\Gamma_{augment}$, to add to the wearer torque response, $\Gamma_{wearer}$, to approximate $\Gamma^*$, the desired normalized biomimetic response.

Figure 9:
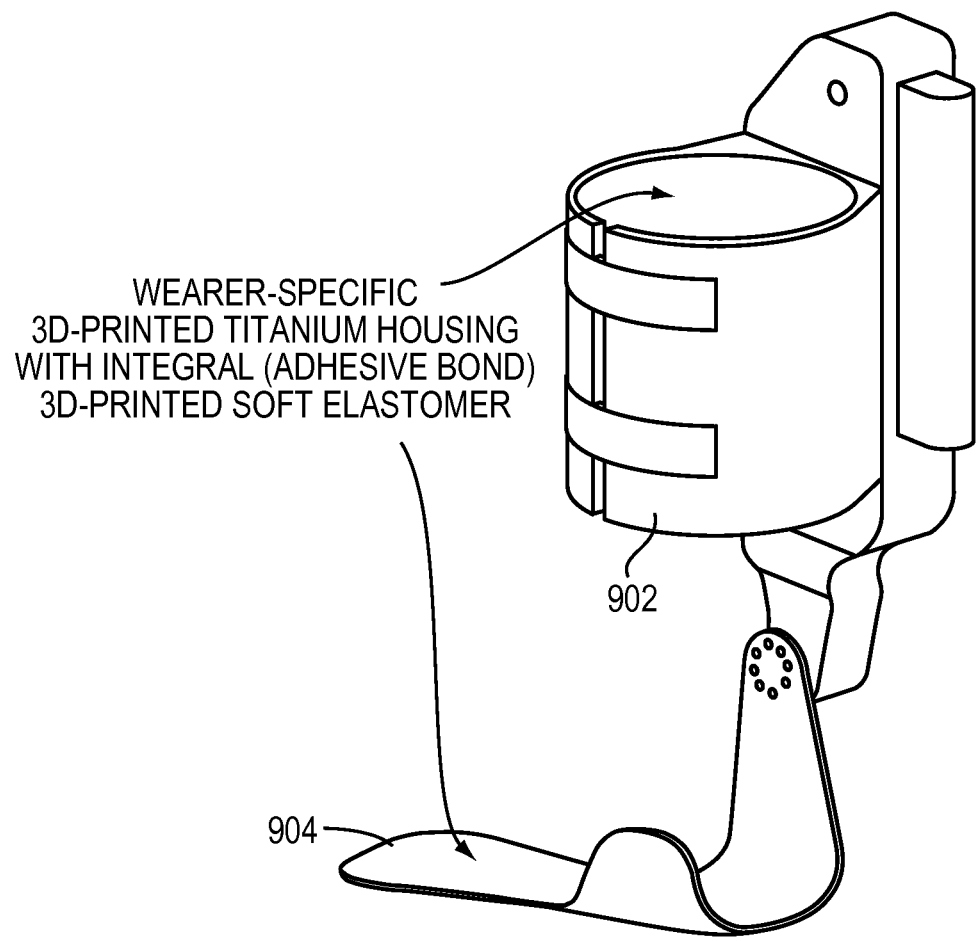
FIG. 9 illustrates seamless integration of a PFO with a lower leg of a human according to one embodiment.

Seamless integration of the Platform 400 or PFO 450 onto a wearer can be important to ensure that the PFO-supplied torque is coupled efficiently. To achieve widespread utility of the wearable robotic technology described herein, a process is developed for custom manufacturing a cuff and foot assembly 902 shown in FIG. 9 that may conform/couple directly to the lower extremity of the wearer. For each wearer 3-D scanning tools measure those body surfaces that integrate with the Platform 400 or PFO 450. From these surface measurements, a direct-write process can print lightweight titanium or carbon-fiber forms that can be functionalized through heat treatment to create the scaffold upon which a custom 3-D printed elastomer 904, with spatially-varying durometer, can be bonded to achieve the desired custom integration.

In some embodiments, the State and Actuator Controller 422 is adapted to kinematically reconstruct a joint path. Such reconstruction can be used to determine the terrain (e.g., whether the terrain is level ground, sloping ground, or stairs), and activity (i.e., whether the wearer is walking on level ground, upslope, or downslope, or walking up or down the stairs). The modulation of the toque, impedance, and joint equilibrium may be based on the terrain and activity as determined via the kinematic reconstruction.

Figure 10:
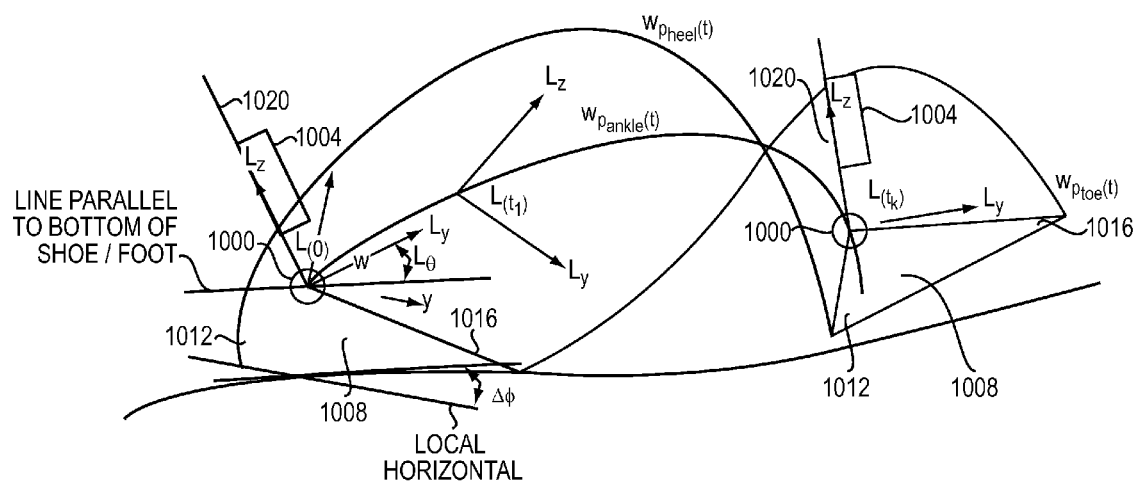
FIG. 10 depicts kinematic reconstruction by a controller for controlling a PFO according to one embodiment.

FIG. 10 illustrates a method for determining, via kinematic reconstruction, ankle joint 1000, heel 1012 and toe 1016 paths while using any PFO (e.g., the Platform 400 or the PFO 450) based on the inertial pose of a lower leg member 1020 coupled to the ankle joint 1000, and the angle between the lower leg member 1020 and foot member 1008. Pose is the position and orientation of a coordinate system. The IMU 424 may be coupled to the lower leg member 1020. The IMU 424 may include a three-axis rate gyro for measuring angular rate and a three-axis accelerometer for measuring acceleration. Placing the inertial measurement unit on the lower leg member 1020 collocates the measurement of angular rate and acceleration for all three axes of the lower leg member 1020. The inertial measurement unit 424 provides a six-degree-of-freedom estimate of the lower leg member 1020 pose, inertial (world frame referenced) orientation and ankle-joint 1000 (center of rotation of the ankle-foot) location.

In some embodiments, the lower leg member 1020 pose is used to compute the instantaneous location of the knee joint. By using knowledge of the ankle joint 1000 angle ($\theta$) the instantaneous pose of the bottom of the foot 1008 can be computed, including location of the heel 1012 and toe 1016. This information in turn can be used when the foot member 1008 is flat to measure the terrain angle in the plane defined by the rotational axis of the ankle joint/foot member. Mounting the inertial measurement unit 424 on the lower leg member 1020 has advantages over other potential locations. Unlike if it were mounted on the foot member 1008, the lower leg member 1020 mounting protects against physical abuse and keeps it away from water exposure. Further, it eliminates the cable tether that would otherwise be needed if it were on the foot member 1008—thereby ensuring mechanical and electrical integrity. Finally, the lower leg member 1020 is centrally located within the kinematic chain of a hybrid system facilitating the computation of the thigh and torso pose with a minimum of additional sensors.

The inertial measurement unit 424 can be used to calculate the orientation, $_{ankle}{}^w O$, position, $_{ankle}{}^w p$, and velocity, $_{ankle}{}^w v$, of the PFO (e.g., Platform 400, the PFO 450, etc.) in a ground-referenced world frame. $_{ankle}{}^w O$ may be represented by a quaternion or by a 3×3 matrix of unit vectors that define the orientation of the x, y and z axes of the ankle joint in relation to the world frame. The ankle joint 1000 coordinate frame is defined to be positioned at the center of the ankle joint axis of rotation with its orientation tied to the lower leg member 1020. From this central point, the position, velocity and acceleration can be computed. For points of interest in, for example, the foot (e.g., the heel 1012 or toe 1016), a foot member-to-ankle joint orientation transformation, $_{foot}{}^{ankle} O(\theta)$ is used to derive the position using the following relation:

$$_{point\text{-}of\text{-}interest}{}^w p = {}_{ankle}{}^w p + {}_{ankle}{}^w O(\gamma)_{foot}{}^{ankle} O(\theta)({}^{foot}\tau_{point\text{-}of\text{-}interest})$$

where $$_{foot}^{ankle} O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix}$$

where γ is the inertial lower lee member angle, and $$_{foot}^{ankle} O(\theta) = \begin{bmatrix} 1 & 0 & 0 \\ 0 & \cos(\theta) & -\sin(\theta) \\ 0 & \sin(\theta) & \cos(\theta) \end{bmatrix}$$

where θ is the ankle joint angle.

In this embodiment, the inertial measurement unit 424, including the three-axis accelerometer and three-axis rate gyro, is located on the forward face at the top of the lower leg member 1020. It is advantageous to remove the effect of scale, drift and cross-coupling on the world-frame orientation, velocity and position estimates introduced by numerical integrations of the accelerometer and rate gyro signals Inertial navigation systems typically employ a zero-velocity update (ZVUP) periodically by averaging over an extended period of time, usually seconds to minutes. This placement of the inertial measurement unit is almost never stationary in the lower-extremity devices such as a PFO. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $^{IMU}a$, the ankle joint acceleration ($^{IMU}a_{ankle}$) is derived with the following rigid body dynamic equation:

$$^{IMU}a_{ankle} = {}^{IMU}a + {}^{IMU}\vec{\omega} \times {}^{IMU}\vec{\omega} \times {}_{ankle}{}^{IMU}\vec{r} + {}^{IMU}\vec{\dot{\omega}} \times {}_{ankle}{}^{IMU}\vec{r}$$

where $^{IMU}\vec{\omega}$ and $^{IMU}\vec{\dot{\omega}}$ are the vectors of angular rate and angular acceleration, respectively, in the inertial measurement unit frame and X denotes the cross-product.

The relationship is solved $_{ankle}{}^w O = {}_{IMU}{}^w O$ similarly as in the equations above using standard strapdown inertial measurement unit integration methods, in accordance with the following relationships known to one skilled in the art:

$$_{ankle}{}^w \dot{\hat{\Phi}} = {}^w\hat{\Omega}({}^w\hat{\omega})_{ankle}{}^w\hat{\Phi}$$

$$^w\dot{\hat{v}}_{ankle} = {}^w\hat{a}_{ankle} - [0,0,g]^T$$

$$^w\dot{\hat{p}}_{ankle} = {}^w\hat{v}_{ankle}$$

$$_{foot}{}^w\hat{\Phi} = {}_{ankle}{}^w\hat{\Phi}_{foot}{}^{ankle}\hat{\Phi} = {}_{ankle}{}^w\hat{\Phi}\,\text{Rotation}_x(\hat{\Theta})$$

$$^w\dot{\hat{v}}_{heel} = {}^w\dot{\hat{v}}_{ankle} + {}^w\hat{\Omega}(_{ankle}{}^w\hat{\Phi}[\hat{\dot{\Theta}}\ 0\ 0]^T){}^w r_{heel\text{-}ankle}$$

$$^w\dot{\hat{v}}_{toe} = {}^w\dot{\hat{v}}_{ankle} + {}^w\hat{\Omega}(_{ankle}{}^w\hat{\Phi}[\hat{\dot{\Theta}}\ 0\ 0]^T){}^w r_{toe\text{-}ankle}$$

$$^w\dot{\hat{p}}_{heel} = {}^w\dot{\hat{p}}_{ankle} + {}^w r_{heel\text{-}ankle}$$

$$^w\dot{\hat{p}}_{toe} = {}^w\dot{\hat{p}}_{ankle} + {}^w r_{toe\text{-}ankle}$$

$$^w r_{heel\text{-}ankle} = {}_{foot}{}^w\hat{\Phi}^{foot}(r_{heel} - r_{ankle})$$

$$^w r_{toe\text{-}ankle} = {}_{foot}{}^w\hat{\Phi}^{foot}(r_{toe} - r_{ankle})$$

In the equations above, the matrix, $\hat{\Phi}$, will be used interchangeably with the orientation matrix, $_{IMU}{}^w O$. The world frame-referenced ankle joint velocity and position are then derived at a point in time after the time of the previous zero-velocity update (i-th zero-velocity update) based on the following:

$$^w v_{ankle}(t) = \int_{ZVUP(i)}^{t} ({}_{IMU}{}^w O)^{IMU} a_{ankle} dt$$

$$^w p_{ankle}(t) = \int_{ZVUP(i)}^{t} {}^w v_{ankle} dt$$

where $^w p_{ankle}(t=ZVUP(i))$ is reset to zero for all i.

Figure 11A:
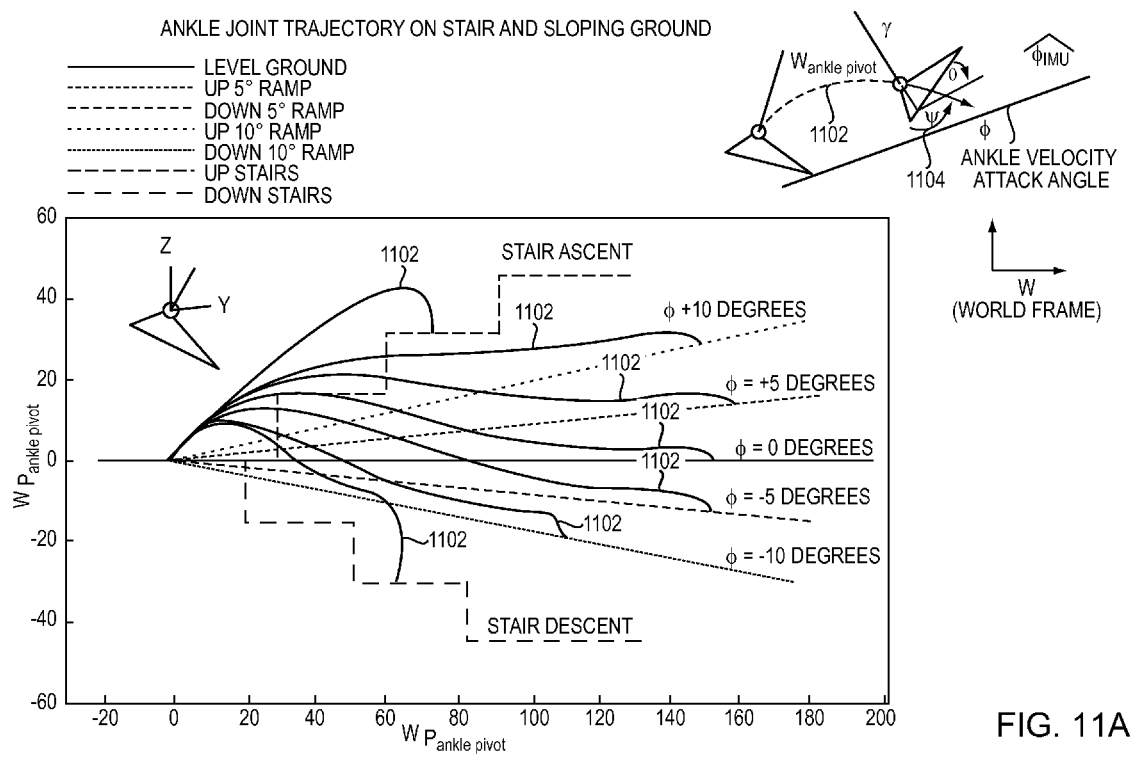
FIGS. 11a and 11b depict ankle and knee paths, respectively, each derived using measurements from an inertial measurement unit, according to one embodiment.

The six-degree-of-freedom inertial measurement unit (IMU) 424 of the Platform 400 or the PFO 450 is capable of computing the path of the ankle joint and the distal-end of the femur (knee) from which the IMU 424 can discriminate and discern terrain modality—including stairs and slopes. With reference to FIG. 11a, inertially referenced ankle joint paths 1102, $^W p_{ankle\ joint}(t)$, and ankle-velocity-attack-angle 1104, $^W V_{ankle\ joint}$, on stairs and sloping ground can be used to discriminate stair ascent/descent from ascent/descent on sloping ground. The slope, φ, can be estimated as $\hat{\phi}$ in swing using the relation:

$$\hat{\phi} = \tan^{-1}({}^W p_{ankle\ joint_z}(t), {}^W p_{ankle\ joint_y})$$

Figure 11B:
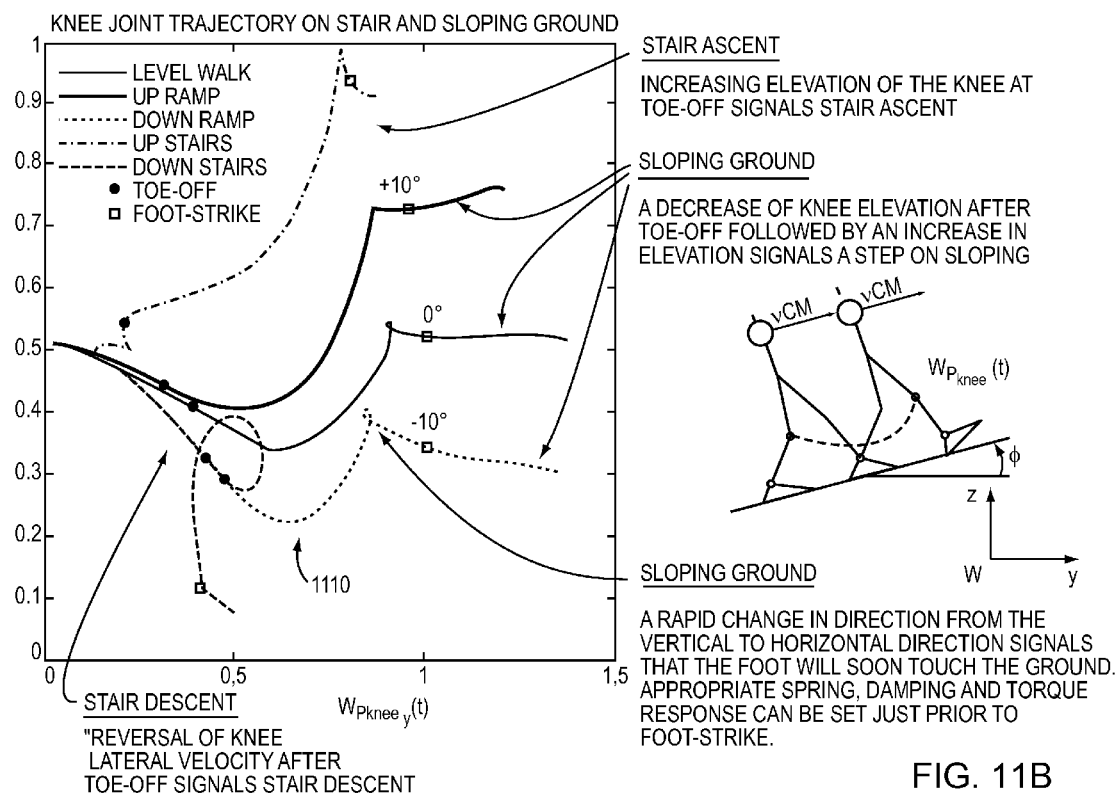

With reference to FIG. 11b, inertially-referenced knee path shape can be used to detect stair ascent/descent shortly after toe-off—enabling knee impedance and torque response to be configured prior to foot-strike on the stair. The "kink" 1110 in the knee path may signal impending foot strike on sloping ground, enabling a prediction of terrain slope using the ankle joint slope prediction described above with reference to FIG. 11a. Using the joint slope, speed and ankle velocity angle-of-attack, the joint equilibrium and impedance can be adjusted in preparation for the foot strike.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A powered device for augmenting a joint function of a human during a gait cycle, the powered device comprising:
    a powered actuator for supplying an augmentation torque and an impedance to a joint; and
    a controller programmed to modulate the augmentation torque, the impedance, and a joint equilibrium according to a phase of the gait cycle to provide at least a biomimetic response, wherein the controller is programmed to:
        compute a normalized biomimetic torque for the phase of the gait cycle, the normalized biomimetic torque according to a speed of ambulation, a terrain, or both a speed of ambulation and a terrain;
        retrieve a state-specific attenuation factor for the phase of the gait cycle;
        scale the normalized biomimetic torque based on the state-specific attenuation factor to determine the augmentation torque; and
        add the augmentation torque to a wearer torque response to approximate the biomimetic response.

2. The device of claim 1, wherein the powered actuator comprises a series-elastic actuator.

3. The device of claim 2, wherein the series-elastic actuator comprises a transverse-flux motor.

4. The device of claim 1, further comprising a first sensor to generate a first sensor signal related to at least one of a terrain and speed of ambulation.

5. The device of claim 4, wherein the controller is adapted to kinematically reconstruct a path of the joint within the gait cycle according to the first sensor signal.

6. The device of claim 5, further comprising an accelerometer to determine heel strike.

7. The device of claim 5, wherein the kinematically reconstructing the path of the joint comprises computing a pose and an origin of a coordinate frame associated with a link connected to at least one of the joint and another joint proximal to the joint.

8. The device of claim 7, wherein computing the pose comprises creating a homogeneous transformation of the coordinate frame.

9. The device of claim 8, wherein the homogeneous transformation comprises:
    a 3×1 vector defining an origin of the coordinate frame; and
    a 3×3 matrix comprising unit vectors of the coordinate frame.

10. The device of claim 7, wherein at least one point within the coordinate frame corresponds to a link connected to at least one of the joint and another joint proximal to the joint.

11. The device of claim 10, wherein the joint is an ankle joint and the at least one point is at least one of a distal end and a proximal end of a tibia connected to the ankle.

12. The device of claim 5, wherein the controller is adapted to determine a terrain type as one of substantially level surface, sloping surface, and stairs.

13. The device of claim 12, wherein the controller is adapted to determine an activity according to the terrain type, the activity being one of ascending stairs, descending stairs, walking on substantially level surface, walking on a surface sloping up, and walking on a surface sloping down.

14. The device of claim 4, further comprising a second sensor to provide a second sensor signal related to at least one of a pitch angle, a pitch velocity, an ankle angle, and joint torque.

15. The device of claim 14, wherein the controller is adapted to determine the phase of the gait cycle based at least in part on the second sensor signal.

16. The device of claim 14, wherein the powered actuator comprises a motor, and the device further comprises a third sensor configured to provide a third sensor signal related to a velocity of the motor.

17. The device of claim 1, further comprising a timer to provide a timing signal to the controller, wherein the controller is adapted to determine the phase of the gait cycle based at least in part on the timing signal.

18. The device of claim 1, wherein the joint equilibrium varies in time during the gait cycle.

19. The device of claim 18, wherein the controller is further programmed to:
    model a joint equilibrium as a second-order response to a joint-position goal to be achieved prior to a next phase of the gait cycle; and
    adjust at least the augmentation torque such that the modeled joint equilibrium is approximately equal to a pre-determined joint equilibrium.

20. The device of claim 19, wherein the second-order response is an over-damped response.

21. The device of claim 1, wherein the biomimetic response is achieved within the gait cycle.

22. The device of claim 1, further comprising an elastic element for applying a torque to the joint, thereby dorsiflexing the joint.

23. The device of claim 1, wherein the joint is an ankle joint.

24. The device of claim 1, wherein the controller is adapted to modulate the augmentation torque according to a positive-force feedback.

25. The device of claim 24, wherein the augmentation torque modulated according to the positive-force feedback in combination with a natural joint torque supplied by the human approximates a normal joint torque.

26. The device of claim 24, wherein the positive-force feedback is adjusted according to at least one of terrain and ambulation speed.

27. The device of claim 1, wherein the controller is adapted to modulate the augmentation torque according to a scaling factor.

28. The device of claim 1, further comprising an external signal to stimulate the powered actuator.

29. The device of claim 1, wherein the controller is programmed to modulate the impedance supplied to the joint by the powered actuator, wherein the impedance is one of linear impedance and non-linear impedance.

* * * * *